United States Patent [19]

Hockney et al.

[11] Patent Number: 5,840,543
[45] Date of Patent: Nov. 24, 1998

US005840543A

[54] FERMENTATION PROCESS

[75] Inventors: Robert Craig Hockney; Bhuphendra Vallabh Kara, both of Cheshire, England

[73] Assignee: Imperial Chemical Industries PLC, London, England

[21] Appl. No.: 431,459

[22] Filed: May 1, 1995

Related U.S. Application Data

[63] Continuation of Ser. No. 215,676, Mar. 22, 1994, abandoned, which is a continuation of Ser. No. 661,306, Feb. 27, 1991, abandoned.

[30] Foreign Application Priority Data

Feb. 27, 1990 [GB] United Kingdom .................... 9004390

[51] Int. Cl.⁶ .............................. C12P 21/02; C12P 21/06
[52] U.S. Cl. .......................................... 435/69.5; 435/69.1
[58] Field of Search ................................ 435/69.1, 69.5, 435/71.1, 71.2, 252.1, 252.3

[56] References Cited

U.S. PATENT DOCUMENTS

| | | | |
|---|---|---|---|
| 4,206,282 | 6/1980 | Hochstein | 435/34 |
| 4,724,206 | 2/1988 | Rupp et al. | 435/69.1 |
| 4,999,291 | 3/1991 | Souza | 435/69.1 |
| 5,122,469 | 6/1992 | Mather et al. | 435/383 |

FOREIGN PATENT DOCUMENTS

| | | |
|---|---|---|
| 0156355 | 10/1985 | European Pat. Off. . |
| 8700195 | 1/1987 | WIPO . |
| 9003430 | 4/1990 | WIPO . |

OTHER PUBLICATIONS

Houtaia et al., Biotechnology Letters, vol. 1, No. 11, 775–778, 1989.

"Manual of Microbiological Methods", Pelczar et al., McGraw–Hill Book Company, Inc., N.Y. (1957) pp. 70–71.

"Glossary of Genetics and Cytogenetics", Green et al., Springer–Verlag, Berlin (1976) p. 43.

*Primary Examiner*—George G. Elliott
*Assistant Examiner*—Terry A. McKelvey
*Attorney, Agent, or Firm*—Cushman Darby & Cushman Intellectual Property Group of Pillsbury Madison & Sutro LLP

[57] ABSTRACT

Processes for preparing polypeptides, such as G-CSF or analogues thereof, in which fermentation is carried out in the presence of at least one amino acid which is present in an amount sufficient to give improved accumulation of the polypeptide. The amino acid may be threonine and/or leucine which is present in the growth medium at a concentration of, for example, about 1.25 to 5 g/l.

18 Claims, 16 Drawing Sheets

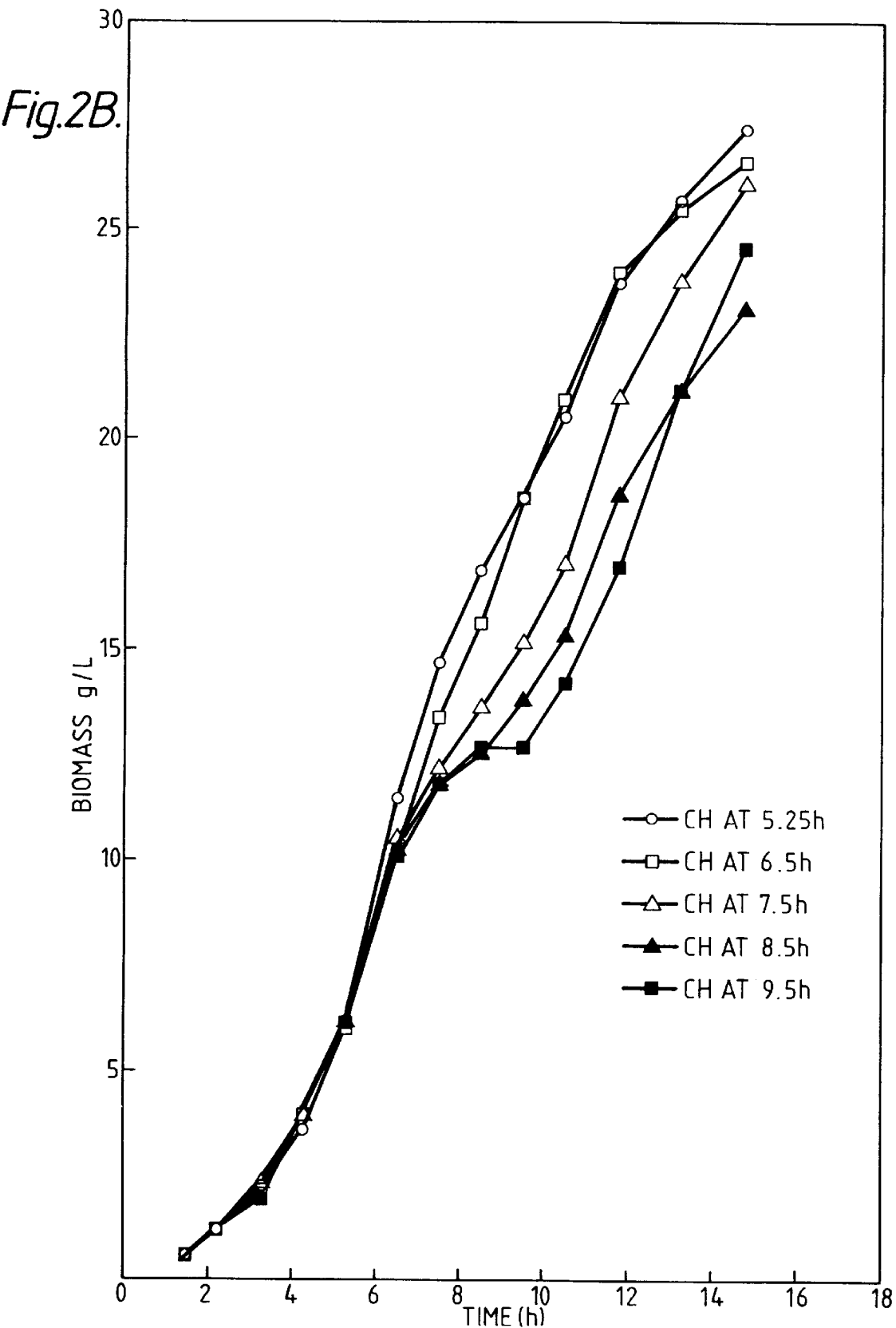

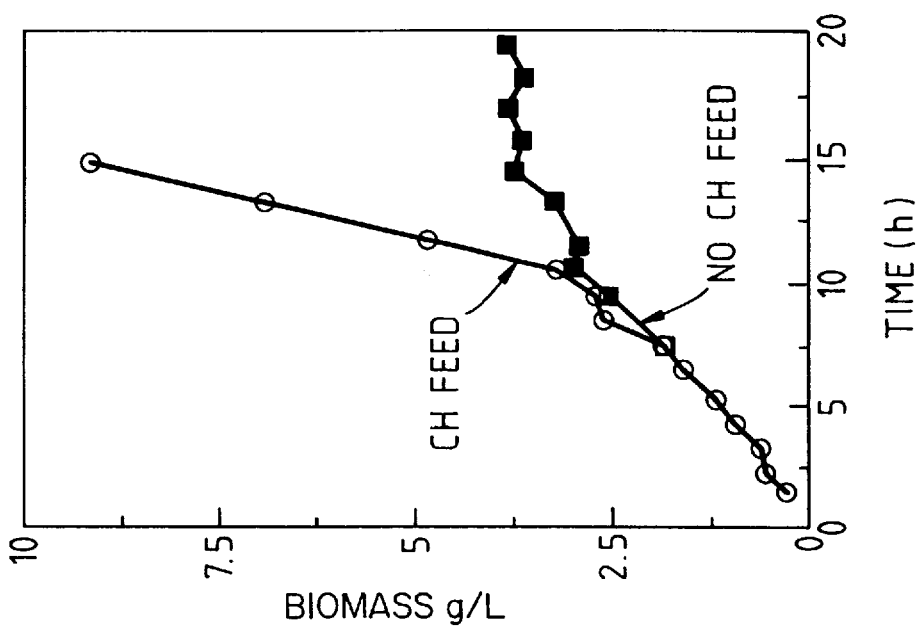
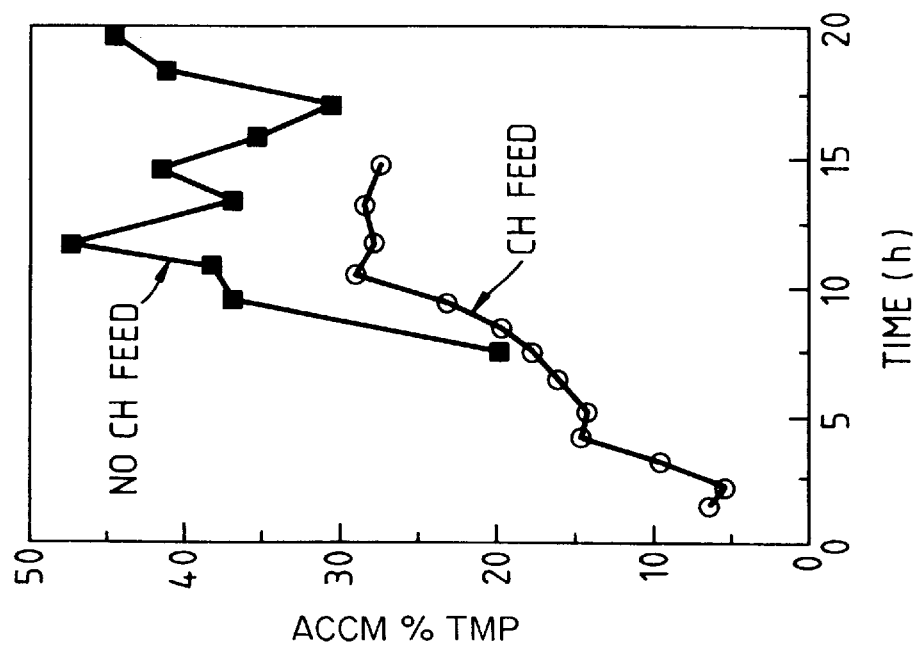

Fig. 5.

EcoRI
AATTCTGGCA AATATTCTGA AATGAGCTGT TGACAATTAA TCATCGAACT

AGTTAACTAG TACGCAAGTT CACGTAAAAA GGGTATCGAC

KpnI    BamHI    XbaI    SalI    PstI    SphI
AATGGTACCC GGGGATCCTC TAGAGTCGAC CTGCAGGCAT GCAAGCTTAG

ClaI/AccI
CCCGCCTAAT GAGCGGGCTT TTTTTTATCG AC

Fig. 8.

TRANSCRIPTION TERMINATION SEQUENCE

SalI
5' TCGACATTATATTACTAATTAATTGGGGACCCTAGAGGTCCCCTTTTTTATTTTAA
3'       GTAATATAATGATTAATTAACCCCTGGGATCTCCAGGGGAAAAAATAAAATT

SphI BamHI  StyI
      AAAGCATGCGGATCCC    3'
      TTTCGTACGCCTAGGGGAAC  5'

Fig. 6A

```
EcoRI    ScaI

AATTCAGT ACT CCA CTG GGT CCA GCA AGC TCT CTG CCG CAG TCT TTC CTG CTG AAG TGT     59
         GTCA TGA GGT GAC CCA GGT CGT TCG AGA GAC GGC GTC AGA AAG GAC GAC TTC ACA
              Thr Pro Leu Gly Pro Ala Ser Ser Leu Pro Gln Ser Phe Leu Leu Lys Cys
                1                    5                   10                  15
                   SnabI                                                   FspI CTC GAA CAG GTA CGT AAA ATT CAA GGC GAT GGT GCG GCT CTG CAG GAA AAG CTG TGC GCA  119
GAG CTT GTC CAT GCA TTT TAA GTT CCG CTA CCA CGC CGA GAC GTC CTT TTC GAC ACG CGT
Leu Glu Gln Val Arg Lys Ile Gln Gly Asp Gly Ala Ala Leu Gln Glu Lys Leu Cys Ala
         20                  25                  30                  35
                    MstII                                       BamHI ACC TAC AAA CTG TGC CAC CCT GAG GAA CTG TGC CTC GGT CAC TCT CTG GGG ATC CCG      179
TGG ATG TTT GAC ACG GTG GGA CTC CTT GAC ACG GAG CCA GTG AGA GAC CCC TAG GGC
Thr Tyr Lys Leu Cys His Pro Glu Glu Leu Val Leu Gly His Ser Leu Gly Ile Pro
         40                  45                  50                  55
           SacI                                       HindIII TGG GCT CCA CTG AGC TCT TGC CCG TCC CAA GCT TTA CAA GTT CGA AAT GTT GAC CGT CCG ACG TCG GTC TGC AGC CAG  219
ACC CGA GGT GAC TCG AGA ACG GGC AGG GTT CGA AAT GTT CGA ACG CGG CAG GCT TTA CAA CTG GCA GGC TGC ACG TCG GTC
Trp Ala Pro Leu Ser Ser Cys Pro Ser Gln Ala Leu Gln Leu Gln Asn Val Asp Arg Pro Leu Ala Gly Cys Leu Ser Gln
             60                  65                  70                  75
                                              XbaI
```

Fig. 6B

```
CTG CAC TCC GGT CTG TTC CTG TAC CAG GGT CTG CTG GCT CTA GAA GGC ATC TCT CCT 299
GAC GTG AGG CCA AAG GAC ATG GTC CCA GAC GTC CGA GAT CTT CCG TAG AGA GGA
Leu His Ser Gly Leu Phe Leu Tyr Gln Gly Leu Leu Ala Leu Glu Gly Ile Ser Pro
            80                    85                    90              95
                                                                        NdeI

GAA TTG GGG CCC ACC CTG GAC ACA CTG CAG CTG GAC GTT GCC GAC TTC GCT ACT ACC ATA 359
CTT AAC CCC GGG TGG GAC CTG TGT GAC GTC GAC CTG CAA CGG CTG AAG CGA TGA TGG TAT
Glu Leu Gly Pro Thr Leu Asp Thr Leu Gln Leu Asp Val Ala Asp Phe Ala Thr Thr Ile
        100                    105                   110                  115

TGG CAA CAG ATG GAG GAA CTG GGT ATG GCT CCG GCA CTG CAG CCG ACT CAG GGT GCG ATG 419
ACC GTT GTC TAC CTC CTT GAC CCA TAC CGA GGC CGT GAC GTC GGC TGA GTC CCA CGC TAC
Trp Gln Gln Met Glu Glu Leu Gly Met Ala Pro Ala Leu Gln Pro Thr Gln Gly Ala Met
    120                    125                   130                   135
                                       BssHII

CCA GCA TTC GCC TCT GCT TTC CAG CGG CGC GCA GGC GGT GTT CTG GTT GCC TCC CAT CTT 479
GGT CGT AAG CGG AGA CGA AAG GTC GCC GCG CGT CCG CCA CAA GAC CAA CGG AGG GTA GAA
Pro Ala Phe Ala Ser Ala Phe Gln Arg Arg Ala Gly Gly Val Leu Val Ala Ser His Leu
        140                    145                   150                   155
    XhoI                                                                 SalI

CAG AGC TTC CTC GAG GTG TCT TAC CGC GTT CTG CGT CAC CTG GCC CAG CCG TAA G      534
GTC TCG AAG GAG CTC CAC AGA ATG GCG CAA GAC GCA GTG GAC CGG GTC GGC ATT CAGCT
Gln Ser Phe Leu Glu Val Ser Tyr Arg Val Leu Arg His Leu Ala Gln Pro
        160                    165                   170       174
```

Fig. 7A

```
EcoRI    ScaI

AATTCAGT ACT CCA CTG GGT CCA GCA AGC TCT CTG CCG CAG TCT TTC CTG AAG TCT    59
         GTCA TGA GGT GAC CCA GGT CGT TCG AGA GGC GTC AGA AAG GAC GAC TTC AGA
              Thr Pro Leu Gly Pro Ala Ser Ser Leu Pro Gln Ser Phe Leu Lys Ser
               1                   5                  10                 15
                    SnabI                                               FspI CTC GAA CAG GTA CGT AAA ATT CAA GGC AGC GGT GCG GCT CTG CAG GAA AAG CTG TGC GCA   119
GAG CTT GTC CAT GCA TTT TAA GTT CCG TCA CGC CGA GAC GTC CTT TTC GAC ACG CGT
Leu Glu Gln Val Arg Lys Ile Gln Gly Ser Gly Ala Ala Leu Gln Glu Lys Leu Cys Ala
            20                  25                  30                  35
                  MstII                                            BamHI ACC TAC AAA CTG TGC CAC CCT GAG GAA CTG CTC GAC CAC GTG CCA CTC GGT CAC TCT CTC GGG ATC CCG   179
TGG ATG TTT GAC ACG GTG GGA CTC CTT GAC GAG CTG GTG CAC GGT GAG CCA GTG AGA GAC CCC TAG GGC
Thr Tyr Lys Leu Cys His Pro Glu Glu Leu Leu Asp His Val Leu Leu Gly His Ser Leu Gly Ile Pro
            40                  45                  50                  55
                SacI                                          HindIII TGG GCT CCA CTG AGC TCT TGC CCG TCC CAA GCT TTA CAA CTG GCA GGC TTG AGC CAG   219
ACC CGA GGT GAC TCG AGA ACG GGC AGG GTT CGA AAT GTT GAC CGT CCG ACG TCG GTC
Trp Ala Pro Leu Ser Ser Cys Pro Ser Gln Ala Leu Gln Leu Ala Gly Cys Leu Ser Gln
            60                  65                  70                  75
                                                       XbaI
```

Fig. 7B

```
CTG CAC TCC GGT CTG TTC CTG TAC CAG GGT CTG CTG CAG GCT CTA GAA GGC ATC TCT CCT  299
Leu His Ser Gly Leu Phe Leu Tyr Gln Gly Leu Leu Gln Ala Leu Glu Gly Ile Ser Pro
                80                      85                      90                      95
                                                                        NdeI

GAA TTG GGG CCC ACC CTG GAC ACA CTG CAG CTG GAC GTT GCC GAC TTC GCT ACT ACC ATA  359
Glu Leu Gly Pro Thr Leu Asp Thr Leu Gln Leu Asp Val Ala Asp Phe Ala Thr Thr Ile
               100                     105                     110                     115

TGG CAA CAG ATG GAG GAA CTG GGT ATG GCT CCG GCA CTG CAG CCG ACT CAG CCG GCG ATG  419
Trp Gln Gln Met Glu Glu Leu Gly Met Ala Pro Ala Leu Gln Pro Thr Gln Pro Ala Met
               120                     125                     130                     135
                                        BssHII

CCA GCA TTC GCC TCT GCT TTC CAG CGG CGC GCG GGT GTT CTG GTT GCC TCC CAT CTT  479
Pro Ala Phe Ala Ser Ala Phe Gln Arg Arg Ala Gly Val Leu Val Ala Ser His Leu
               140                     145                     150                     155
               XhoI                                                             SalI

CAG AGC TTC CTC GAG GTG TCT TAC CGC GTT CTG CGT CAC CTG GCC CAG CCG TAA G  534
Gln Ser Phe Leu Glu Val Ser Tyr Arg Val Leu Arg His Leu Ala Gln Pro
               160                     165                     170      174
```

FERMENTATION PROCESS

This is a continuation of application Ser. No. 08/215,676 filed on Mar. 22, 1994 (abandoned) which is a continuation of Ser. No. 07/661,306 filed on Feb. 27, 1991 (now abandoned).

This invention relates to a process for producing a polypeptide, and to a composition suitable for use in producing a polypeptide.

A large number of chemical substances are synthesised, metabolised, accumulated in the cell, or excreted into the fermentation medium during the life of a microbial culture. The discovery that some of these substances possessed utility as foodstuffs or pharmaceuticals led to growth of the fermentation industry. In recent years the role of fermentation has increased in importance due to the advent of genetic engineering since substances which are difficult or even impossible to prepare by conventional chemical means may be prepared by fermentation of an appropriately genetically engineered micro-organism.

Often several different media will support the growth of a cell culture. Generally, the growth medium components are chosen so that the medium provides a nutritional environment in which the cells can grow. The basic composition of a growth medium is: a suitable nitrogen source, such as ammonia, nitrate, or an amino acid; a suitable carbon source, such as glucose, maltose, lactose or glycerol; an inorganic phosphate; and trace elements, such as iron, manganese, zinc, molybdenum and copper. Typically, in the case of industrial fermentations these constituents are replaced by less expensive materials. For example, a nitrogen source of corn-steep liquor, yeast extract, vegetable protein, fishmeal or a protein hydrolysate is often used, and starches, dextrins, molasses and sugar syrups are used as a carbohydrate source. In addition, some strains of organism, termed auxotrophs, require specific substances (or growth factors) for survival not needed by the wild type. Thus, in the case where an auxotroph is used the growth medium has to be supplemented with the appropriate substance.

Fermentation processes may be used to produce a number of chemical substances, for example polypeptides which possess pharmacological activity. However, in many cases the level of accumulation is low, thus in practice the substance may be difficult or impossible to obtain.

A process for producing glyceraldehyde-3-phosphate dehydrogenase using *E.coli* C 600 gal K (lac$^-$, thr$^-$, leu$^-$, thia$^-$) and a medium enriched with threonine and leucine has been reported by N. EL HOUTAIA et al (Biotechnology Letters Vol 1, No 11, 775–778, 1989). It was observed that when the medium was enriched with threonine and leucine at a concentration of 0.1 to 0.3 g/l, that is with the main auxotrophies of the strain, an increase in production occurred. There is reported to be no effect above 0.3 g/l.

The present invention is based on the discovery that when certain amino acids are present in a fermentation process improved accumulation of the desired metabolite may be obtained.

According to the present invention there is provided a process for preparing a polypeptide, said method comprising cultivating a host transformed with a vector or plasmid carrying genetic material coding for said polypeptide in the presence of at least one amino acid which is present in an amount sufficient to give improved accumulation of the polypeptide and which is not an auxotroph of the host.

According to the present invention there is also provided a process for preparing a polypeptide, said method comprising cultivating a host transformed with a vector or plasmid carrying genetic material coding for said polypeptide in the presence of a growth medium and adding a supplement comprising at least one amino acid which is present in an amount sufficient to give improved accumulation of the polypeptide.

The supplement comprises at least one amino acid such that the amount present is the growth medium is sufficient to give improved accumulation of the polypeptide.

The supplement may be added at the start of the cultivation process or after the start of the cultivation process.

It is preferred that the amino acid(s) inhibits growth of the host.

The amino acid(s) is/are advantageously present in an amount which is elevated with respect to know growth media, that is the ratio of the amino acid(s) to other amino acids in the growth medium is greater than that in growth media which form part of the state of the art. Thus, the amount of the amino acid(s) employed renders the growth medium out of balance with respect to the said amino acid(s).

The host and the amino acid(s) are conveniently selected such that the amino acid(s) is not essential for survival of the host, that is the host is not an auxotroph which requires the amino acid(s) or its survival.

Preferably, the host is a prototroph. For example the host may comprise a wild strain which is a prototroph.

The host may comprise a bacterial host, for example *E.coli*; a yeast host, for example saccharomyces cerevisiae; or a mammalian host.

When a bacterial host, such as *E. coli* is employed, the process is generally carried out at at a temperature of about 37° C. and at a pH of about 6.8.

The amino acid(s) may comprise leucine and/or threonine. Preferably, the amino acid(s) is leucine. As indicated above, the amount of threonine and/or leucine is elevated with respect to that in growth mediums which form part of the state of the art and the growth medium is hence out of balance for leucine and/or threonine. The amino acid(s) may comprise threonine and/or leucine which is, or are each, present in a concentration range of about 1.25 to 5 g/l (inclusive), preferably about 2.5 g/l. Conveniently, the amino acid(s) comprises leucine which is present in a concentration in the range of about 1.25 to 5 g/l (inclusive), and is most preferably present at a concentration of about 2.5 g/l.

The process may be carried out in any growth medium known in the art.

Conveniently, the polypeptide comprises human G-CSF or an analogue thereof.

BRIEF DESCRIPTION OF THE DRAWINGS

FIGS. 2A–2B show accumulation and cell growth in the fermentation process of Example 4 with a rate of 1.5 g/L/h but commencing at different times.

FIGS. 4A–4B show accumulation and cell growth in the fermentation process of Example 5.

FIG. 5 shows the nucleotide sequence (SEQ ID NO:28) consisting of a synthetic *E. coli* trp promoter and trp leader ribosome binding site, a translation initiation codon, a multiple restriction enzyme recognition sequence derived from M13mp18, and a synthetic transcription termination sequence.

FIGS. 6A–6B show the nucleotide and amino acid sequences of human G-CSF (SEQ ID NOS:29 and 31).

FIGS. 7A–7B show the G-CSF gene sequence (SEQ ID NO:29) cloned into plasmid vector pICI0020.

FIG. 8 shows the nucleotide sequence of the double-stranded transcription terminator (SEQ ID NOS:34 and 35).

Figure 1:
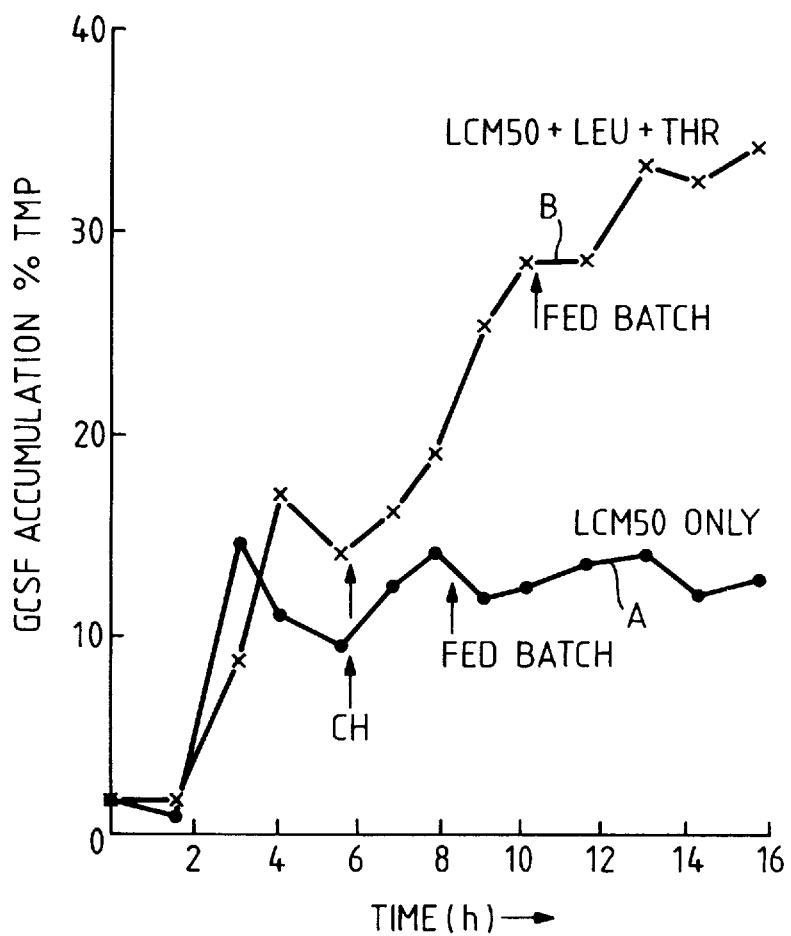
FIG. 1 shows G-CSF accumulation as a function of time for the case where the growth medium was LCM50 (A) and where the growth medium was LCM50 supplemented with leucine and threonine (B).
Figure 2A:
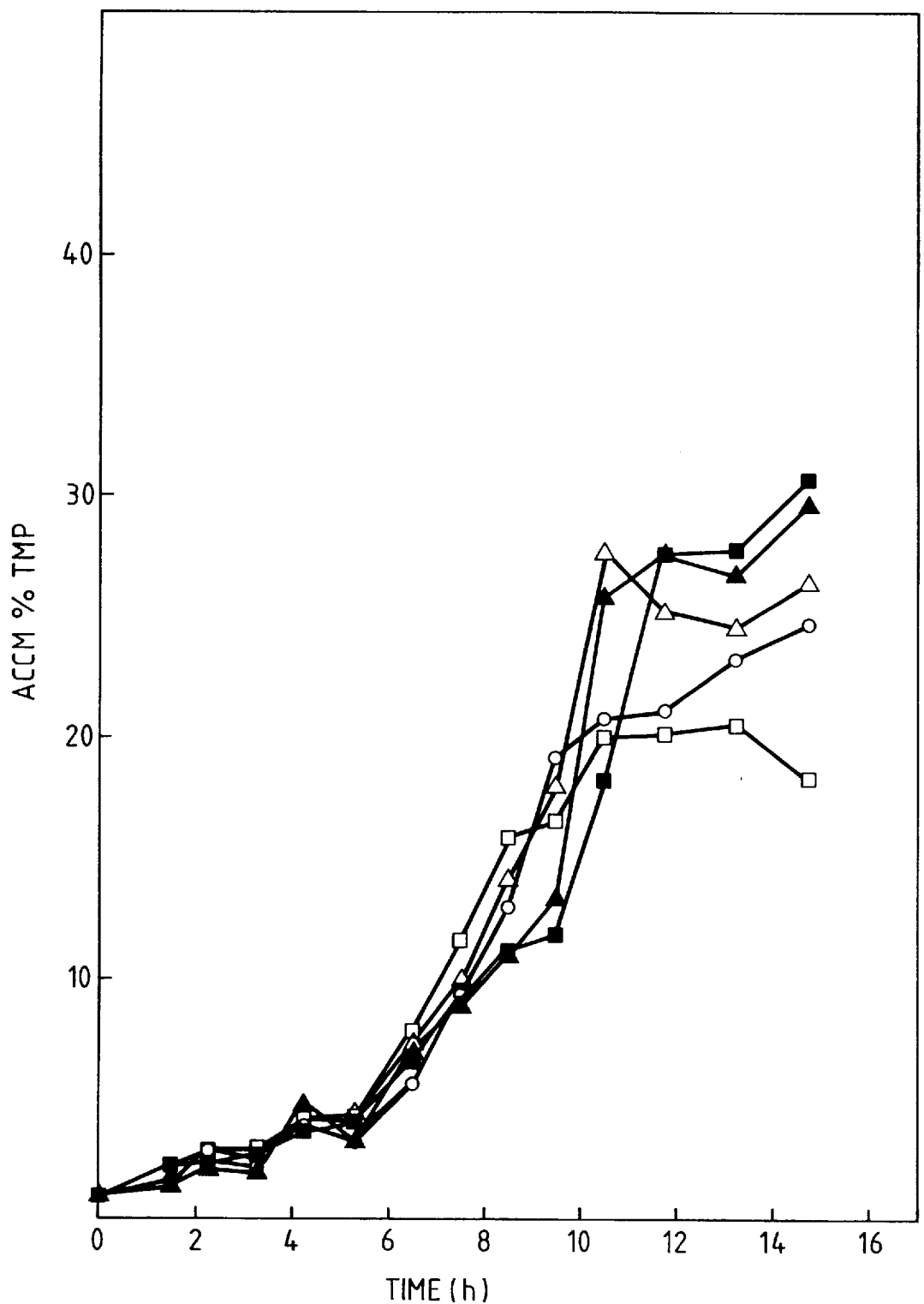
Figure 3A:
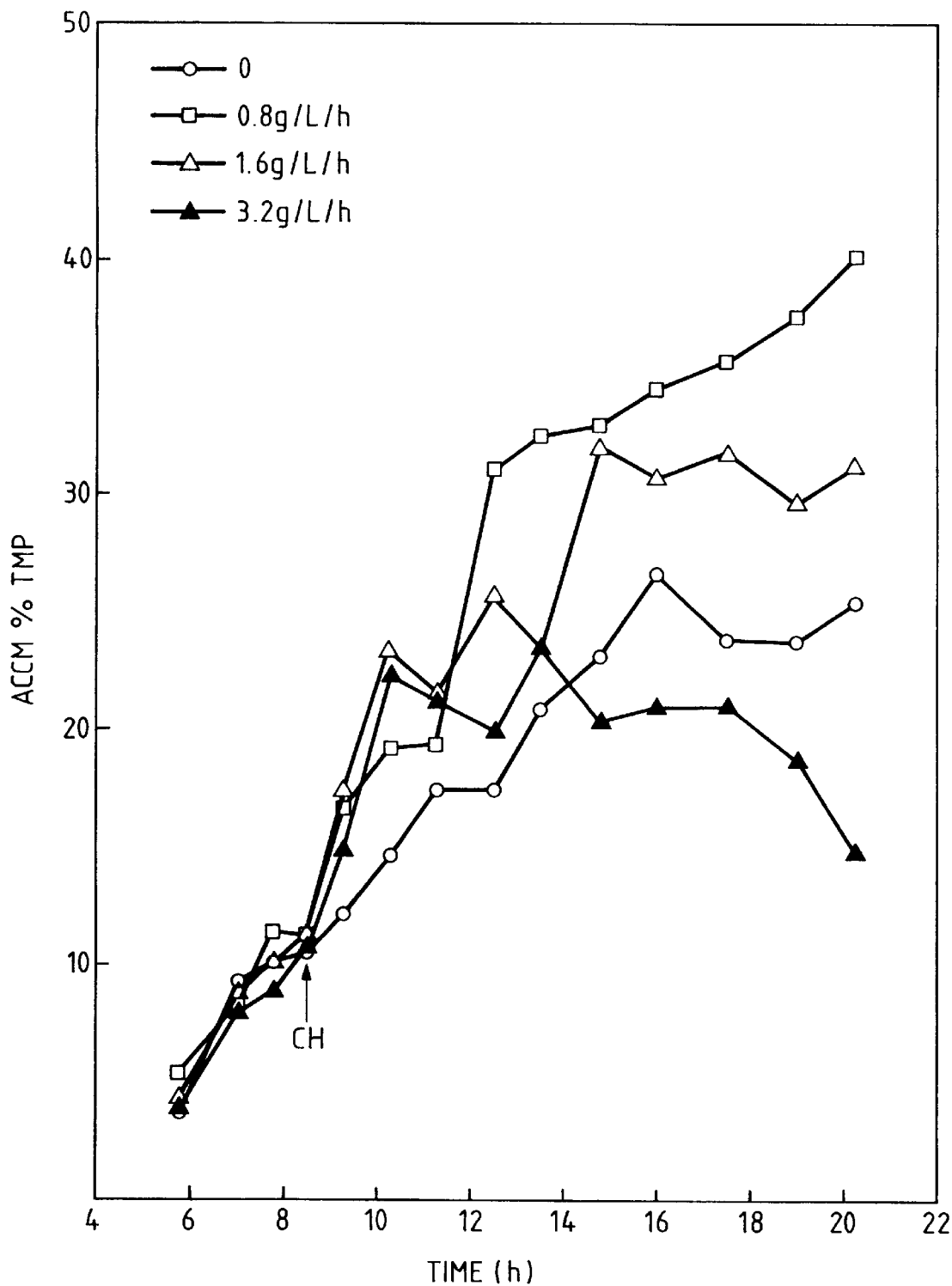
FIGS. 3A–3B show accumulation and cell growth in the fermentation process of Example 4 commencing at different times but at different rates.
Figure 3B:
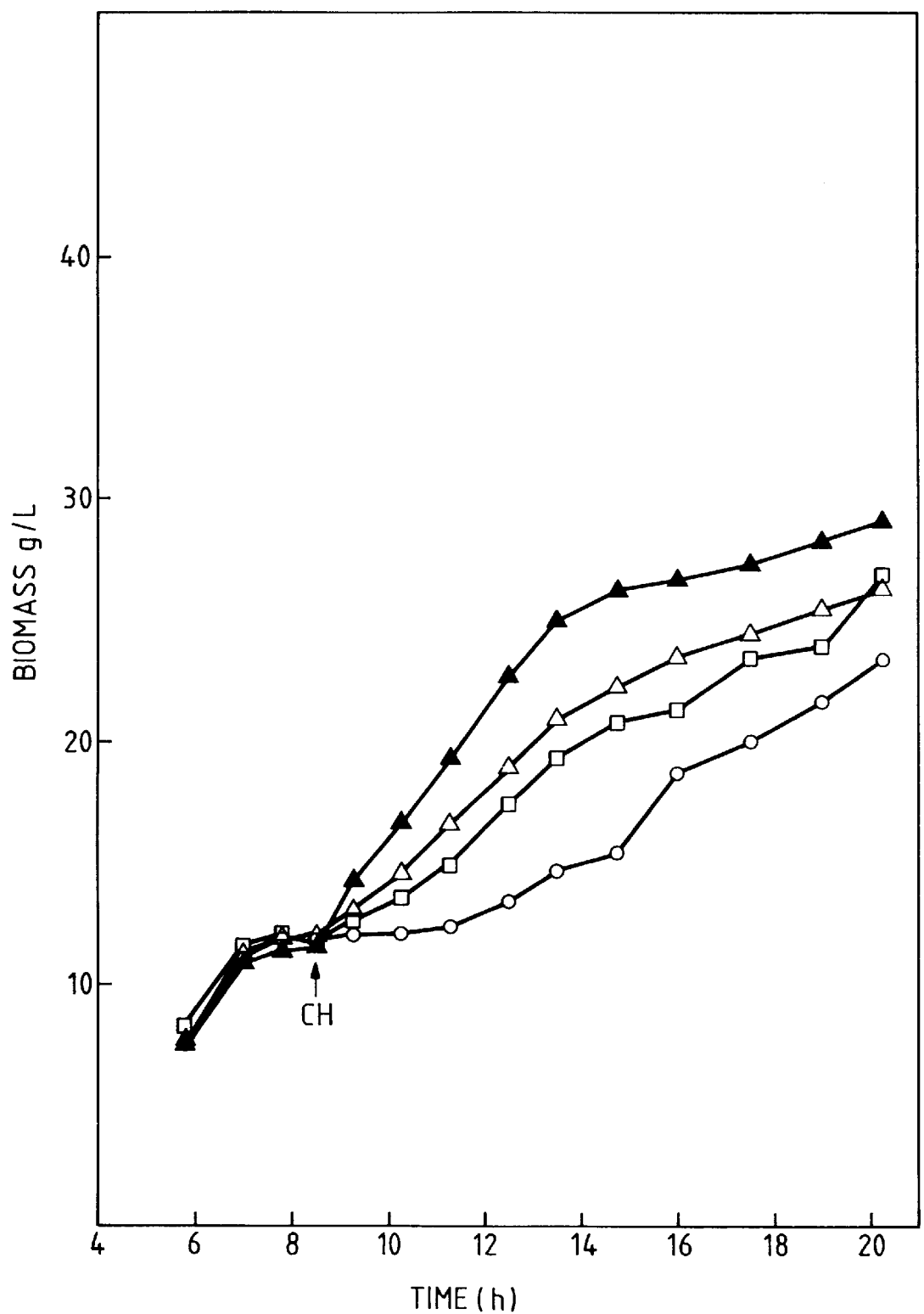

Granulocyte colony stimulating factor (G-CSF) has been described in the literature by Wallet K. et al Proc. Natl. Acad. Sci. USA Vol 82, pp 1526–1530 and has also been described in European Patent Publication No 169,566 and PCT Patent Publication No WO 87/01132. G-CSF has been shown to stimulate granulocyte production in vivo and to function with minimal side effects. As a result human G-CSF is seen as having potential utility in the management of neutropaenia associated with chemotherapy, radiation therapy, radiation accident or autologous bone marrow transplantation. Moreover G-CSF may have utility in the stimulation of bone marrow suppression associated with AIDS, in the treatment of myelodysplastic syndromes characterised by granulocyte functional abnormalities and as an adjunct to the treatment of severe infections.

The term "human G-CSF" as used herein refers to those G-CSFs that have been found to exist in nature and includes the two polypeptides having the amino acid(s) sequence set out in SEQ ID NOS: 30 and 31. These two polypeptides differ only in so far as a tripeptide insert Val-Ser-Glu is present in one polypeptide between positions 35 and 36, but absent in the other. The numbering used throughout the present specification is based on the naturally occurring polypeptide without the Val-Ser-Glu insert.

Analogues of G-CSF include polypeptides which differ from that of naturally occurring G-CSFs in terms of the identity or location of one or more amino acid residues. For example, such analogues may contain substitutions, or terminal or intermediate additions or deletions of such residues. Such analogues would share the property of naturally G-CSFs of being able to stimulate granulocyte production.

In a preferred embodiment of the present invention, a polypeptide is prepared by cultivating a host comprising an *E. coli* strain which is a prototroph and which is transformed with a vector or plasmid carrying genetic material coding for said polypeptide in the presence of an amount of leucine and/or threonine sufficient to inhibit growth of the host and lead to improved accumulation of the polypeptide.

A substance which stimulates growth of the host may be present, for example casein hydrolysate or isoleucine.

According to the present invention there is also provided a composition suitable for use as a growth medium for fermentation processes, said composition including threonine and/or leucine.

The amount of threonine and/or leucine is conveniently elevated with respect to growth media already known in the art, and is advantageously present in an amount sufficient to give improved accumulation of the desired fermentation product. The composition may include, for example threonine and/or leucine which is (or are each) present in a concentration of about 1.25 to 5 g/l (inclusive), preferably 2.5 g/l. Preferably, the composition includes leucine, which may be present in the range of about 1.25 or 5 g/l (inclusive), and is most preferably present at a concentration of about 2.5 g/l.

According to the present invention there is also provided a fermentation process, said process comprising cultivating a host in the presence of at least one amino acid which inhibits growth of the host and gives improved accumulation of the desired metabolite.

The amino acid(s), and the host may comprise those stated above.

The process may be employed to prepare a polypeptide such as G-CSF or an analogue thereof.

The process of the present invention gives improved accumulation of the desired metabolite.

The results obtained are particularly surprising where the amino acid is not an auxotroph of the host.

The polypeptide produced may be recovered and purified by methods well known in the art. For example, purification of G-CSF (and analogues) may be carried out using the procedure set out on pages 48 and 49 of PCT Patent Publication No. WO 87/01132 with final dialysis being effected against phosphate buffered saline.

The invention will now be further described, by way of example only, with reference to the following Examples.

EXAMPLE 1

*E. coli* strain CGSC 6300 obtained from the *E. coli* Genetic Stock Centre was transformed with plasmid pICI 1056 which expresses human G-CSF from a tryptophan promoter. The resultant strain CGSC 6300 (pICI 1056) was purified and maintained in glycerol stocks at −80° C.

An aliquot of the culture was removed from stock and streaked onto agar plates of L-ampicillin-to separate single colonies after overnight growth at 37° C.

A single colony of CGSC 6300 (pICI 1056) was removed and resuspended in a 10 ml L-ampicillin broth and 100 $\mu$l immediately inoculated into each of 20 250 ml Erlenmeyer flasks containing 75 ml L-ampicillin broth. After growth for 16 h at 37° C. on a reciprocating shaker the contents of the flasks were pooled. Half of the volume was used to inoculate a fermenter containing LCM50 growth medium (see table 1) and half used to inoculate a fermenter containing LCM50 medium which had been supplemented with leucine (2.5 g/l) and threonine (0.9 g/l).

The two fermentations were then carried out identically at a temperature of 37° C. and pH, controlled by automatic addition of 6M sodium hydroxide solution, of pH 6.7. The dissolved oxygen tension (dOT) set point was 50% air-saturation and was initially controlled by automatic adjustment of the fermenter stirrer speed. Air-flow to the fermenter was 50l/min, corresponding to 2.5 volume volume per minute (VVM) throughout. Since the oxygen transfer rate (OTR) of the fermenters was unable to meet the oxygen uptake rate (OUR) of the bacteria at a cell density greater than that corresponding to an $OD_{550}$ of 50 under the conditions described, dOT in the fermenter at cell densities greater than this was maintained at 50% air-saturation by restricting bacteria oxygen uptake rate. This was achieved by formulating the medium to become carbon-limited at $OD_{550}$ of 50 and then supplying a feed of the limiting carbon source, together with ammonium sulphate and yeast extract, at a rate which restricted bacterial growth rate.

Fermentations were performed for 16 h and during that time samples were taken for measurement of optical density (OD$_{550}$), cell dry weight and accumulation of G-CSF within the cells. G-CSF accumulation was measured by scanning Coomassie blue stained SDS-PAGE gels of whole cell lysates of the sampled bacteria as is well known in the art.

When OD550 reached 25, casein hydrolysate solution (100 g/l Oxoid L41) was fed pumped into the fermenters at a rate of 1.5 g/l/h.

When OD550 reached approximately 50, the supply of carbon-source in the fermentation batch became exhausted leading to a rapid rise in dOT from 50% air saturation. At this point, a feed containing glycerol (470 g/l), yeast extract (118 g/l) and ammonium sulphate (118 g/l) was pumped into the fermenters at a rate which returned and then maintained the dOT at 50% air saturation.

Except for the addition of leucine (2.5 g/l) and threonine (0.9 g/l) to one fermenter prior to inoculation, the medium and fermentation conditions for the two fermenters were identical.

The addition of leucine and threonine to the fermentation produced an unexpected improvement in the accumulation of G-CSF. This effect is illustrated in FIG. 1 which shows the G-CSF accumulation as a function of time for the case where the growth medium was LCM50 (curve A) and where the growth medium was LCM50 supplemented with leucine and threonine (curve B).

TABLE 1

Composition of LCM50

| | Made up of distilled water g/l |
|---|---|
| KH$_2$PO$_4$ | 3.0 |
| Na$_2$HPO$_4$ | 6.0 |
| NaCl | 0.5 |
| Casein hydrolysate (Oxoid L41) | 2.0 |
| (NH$_4$)$_2$SO$_4$ | 10.00 |
| Yeast Extract (Difco) | 10.00 |
| Glycerol | 35 |
| MgSO$_4$.7H$_2$O | 0.5 |
| CaCl$_2$.2H$_2$O | 0.03 |
| Thiamine | 0.008 |
| FeSO$_4$/Citric Acid | 0.04/0.02 |
| Trace element solution (TES) | 0.5 ml |

EXAMPLE 2

The fermentation process described in Example 1 was repeated with a growth medium supplement containing various concentrations of leucine and/or threonine. Table 2 shows the final accumulation of G-CSF in each case and compares the accumulation obtained with that obtained in the case where the LCM50 growth medium was not supplemented (see Example 1)

SUPPLEMENT MADE TO LCM50 (g/l)

| Leucine | Threonine | BIOMASS (g/l) | G-CSF ACCUMULATION % total microbial protein |
|---|---|---|---|
| None | None | 35 | 11 |
| 2.5 | 0.9 | 24 | 35 |
| 0.9 | 2.5 | 25 | 28 |
| 0.9 | None | 25 | 22 |
| 2.5 | None | 27 | 32 |
| None | 0.9 | 37 | 15 |

SUPPLEMENT MADE TO LCM50 (g/l)

| Leucine | Threonine | BIOMASS (g/l) | G-CSF ACCUMULATION % total microbial protein |
|---|---|---|---|
| None | 2.5 | 29 | 18 |
| Arginine (2.5 g/l) | | 37 | 13 |

EXAMPLE 3

The fermentation process of Example 1 was repeated, but an E. coli strain CGSC 6300 transformed with a plasmid pICI 1197 was used in place of CGSC 6300 transformed with plasmid pICI 1056. Plasmid pICI 1197 expresses an analogue of human G-CSF from a tryptophan promoter. The fermentation was carried out in growth medium LCM50 with a supplement containing varying concentrations of leucine, but no threonine, and also in the absence of supplement (for comparison). Table 3 illustrates the results obtained.

| LEUCINE SUPPLEMENT TO LCM50 (g/l) (NO THREONINE) | Accumulation % TMP | BIOMASS g/l |
|---|---|---|
| NONE | 8 | 38 |
| 0.3125 | 19 | 26 |
| 0.625 | 27 | 25 |
| 1.25 | 25 | 26 |
| 2.50 | 26 | 25 |
| 5.0 | 27 | 26 |
| 2.5 g/l Leu/0.9 g/l thr | 26 | 27 |

(TMP stands, for total microbia protein)

EXAMPLE 4

The fermentation process of Example 3 was repeated using a growth medium of LCM50 and a supplement containing leucine (0.625 g/L) to stimulate accumulation. Casein hydrolysate feed was supplied.
a) at 1.5 g/L/h, but commencing at different times; and
b) commencing at a fixed time, but at different rates.

The changes in cell growth and accumulation were monitored and are illustrated in FIGS. 2A–B and 3A–B.

EXAMPLE 5

The fermentation process of Example 3 was repeated using a growth medium of LCM50, but with the yeast extract omitted, and a supplement of leucine (0.625 g/L) in the case where a casein hydrolysate feed was employed and in the case where a casein hydrolysate feed was not employed. The results are illustrated in FIGS. 4A–B.

It is believed, though we do not wish to be bound by this theory, that the leucine and/or threonine inhibits growth of the host.

Also, it will be appreciated that the quantities of leucine and/or threonine employed may be varied and that by using a smaller amount of leucine/threonine a lower level of accumulation may be obtained, whilst if a higher level of accumulation is desired, the amount of leucine/threonine may be increased.

PREPARATION OF PLASMIDS

The plasmids referred to above were prepared by the procedure described below. Details of the "GENECLEAN"

"SEQUENASE" and Random Labelling Kits referred to below are as follows.
"GENECLEAN"
The kit contains 1) 6M sodium iodide 2) a concentrated solution of sodium chloride, Tris and EDTA for making a sodium chloride/ethanol/water wash; 3) "GLASSMILK"—a 1.5 ml vial containing 1.25 ml of a suspension of silica matrix in water.

This is a technique for DNA purification based on the method of Vogelstein and Gillespie published in Proceedings of the National Academy of Sciences USA (1979) Vol 76, p 615.

Alternatively any of the methods described in "Molecular Cloning—a laboratory manual" Second Edition, Sambrook, Fritsch and Maniatis (Cold Spring Harbor Laboratory, 1989) can be used.
Random Label Kit Product of Pharmacia No 27-9250

The procedure is described in "Molecular Cloning—a Laboratory Manual" Second Edition, Sambrook, Fritsch and Maniatis, pp 10.13–10.17 (Published by Cold Spring Harbor Laboratory 1989).
"SEQUENASE"
Chemically modified T7 DNA polymerase
Based on the procedure of Tabor and Richardson published in "Proceedings of the National Academy of Sciences USA (1987) vol 84 pp 4767–4771.

PREPARATION OF pICI 1056 a) Preparation of a synthetic gene for human G-CSF

A DNA sequence (FIG. 6) encoding the amino acid(s) sequence of the polypeptide of FIG. 6 (human G-CSF) was designed according to the following considerations:

1) Single-stranded cohesive termini to allow ligation at suitable sites in a plasmid.
2) A series of restriction endonuclease sequences throughout the gene to facilitate subsequent genetic manipulation.
3) Translation termination codon.
4) Codons at the 5'-end of the coding region were normally chosen to be A/T rich. Other codons were normally chosen as those preferred for expression in E.coli.

The gene was assembled from the 18 oligonucleotides designated SEQ ID NOS: 1–18 and shown hereinafter.
Preparation of Oligonucleotides The oligonucleotide sequences shown hereinafter were prepared on an Applied Biosystems 380A DNA synthesiser from 5'-dimethoxytrityl base-protected nucleoside-2-cyanoethyl-N,N-diisopropylphosphoramidites and protected nucleosides linked to controlled-pore glass supports on a 0.2 micro mol scale, according to protocols supplied by Applied Biosystems Inc.

Alternatively, the oligonucleotide sequences may be prepared by manual methods as described by Atkinson and Smith in 'Oligonucleotide Synthesis, a Practical Approach' (M. J. Gait, Editor, IRL Press, Oxford, Washington D.C., pages 35–81).

In detail, the preparation of the oligonucleotide sequences by use of the Applied Biosystems 380A DNA synthesiser was effected as follows:

Each oligonucleotide, after cleavage from the solid support and removal of all protecting groups, was dissolved in water (1 ml). A solution of 3M sodium acetate (pH5.6; 40 μl) and ethanol (1 ml) was added to the oligonucleotide solutions (400 μl) and the mixtures stored at −70° C. for 20 hours. The resulting precipitates were collected by centrifugation (13,000 rpm for 10 minutes) and the pellets washed with ethanol:water (7:3) (200 μl) then dried briefly in vacuo and dissolved in water (15 μl) and 10 μl of a formamide/dye mix. (10 mM NaOH, 0.5 mM EDTA, 0.01% Bromophenol Blue, 0.01% xylene cyanol, 80% formamide.

The oligonucleotides were purified on a 10% polyacrylamide gel in 50 mM Tris-borate (pH8.3) containing 8.3M urea. Oligonucleotides of correct length were identified by UV shadowing (Narang et al., 1979 in Methods in Enzymology Vol 68, 90–98)—normally the most prominent band—excised from the gel and electroeluted in 5 mM tris-borate (pH 8.3) at 300 mV for 3–4 hours. The aqueous solutions were concentrated to about 200 μl by treatment with n-butanol (mix, spin and removal of the upper organic layer). The purified oligonucleotides were precipitated at −70° C. for 20 hours from a 0.3M sodium acetate solution by addition of ethanol (2.5 volumes).

Assembly of gene

Oligonucleotides SEQ ID NOS: 2 to 17 (400 pM of each) [as defined hereinafter] were phosphorylated with T4 polynucleotide kinase (3.6 units) for 2 hours at 37° C. in 25 μl of a solution containing ATP (800 pM containing 25 pM gamma-$^{32}$P ATP), 100 μM spermidine, 20 mM MgCl$_2$, 50 mM Tris-HCl (pH9.0) and 0.1 mM EDTA. The solutions were heated at 100° C. for 5 minutes to terminate the reactions, then mixed in pairs as shown in Table 1 to give duplexes A to I (Oligonucleotides SEQ ID NO: 1 and SEQ ID NO: 18 (400 mM in 25 μl) were used unphosphorylated). 0.3M Sodium acetate (pH5.6, 200 μl) and ethanol (850 μl) were added and the duplexes precipitated at −20° C. for 20 hours. The resulting precipitates were collected by centrifugation and washed with ethanol:water (7:3) then dissolved in water (50 μl). The pairs of oligonucleotides were annealed together by first heating the solutions to 100° C. for 2 minutes in a boiling water bath. The bath was then allowed to cool slowly to 40° C. (about 4 hours). Solutions containing 3 pairs of duplexes were combined as shown (see Table 4), to give groups I to III lyophilised and dissolved in 30 μl of a solution containing T4 DNA ligase (1 unit; BRL), 50 mM Tris (pH7.6), 10 mM magnesium chloride, 5% (w/v) PEG 8000, 1 mm ATP, 1 mm DTT. (BRL, Focus Vol 8 no 1 Winter 1986) and the DNA ligated at 30° C. for 5 minutes followed by 20 hours at 16° C. 3M Sodium acetate (20 μl) and water (150 μl) was added and the product precipitated by addition of ethanol (750 μl) and cooling to −20° C. for 20 hours. The precipitate was collected by centrifugation and washed with ethanol (1 ml) then dissolved in water (15 μl) and formamide/dye mix (10 μl) and purified on a 10% polyacrylamide gel in 50 mM Tris-borate (pH8.3), 1 mM EDTA and 8.3M urea. Bands for strands of appropriate lengths (173–186 bases) were identified by autoradiography and isolated together by electroelution from a single gel slice as described above for individual oligonucleotide sequences. The DNA strands were annealed by first heating an aqueous solution (50 μl) at 100° C. for 2 minutes, then allowing it to cool to 40° C. over 4 hours.

Groups I, II and III were ligated together essentially as described for the group preparation to give as the product, the gene sequence shown in FIGS. 6A–B. After precipitation, the gene was phosphorylated with T4 polynucleotide kinase as described previously for individual oligonucleotides, then dissolved in water (20 μl).

TABLE 4

| OLIGO-DUPLEX | NUCLEOTIDE | NUMBER OF BASES IN TOP STRAND | BOTTOM STRAND |
|---|---|---|---|
| A | SEQ ID NO:1 + SEQ ID NO:2 | 62 | 64 |
| B | SEQ ID NO:3 + SEQ ID NO:4 | 60 | 60 |
| C | SEQ ID NO:5 + SEQ ID NO:6 | 48 | 51 |
| D | SEQ ID NO:7 + SEQ ID NO:8 | 63 | 60 |
| E | SEQ ID NO:9 + SEQ ID NO:10 | 63 | 63 |
| F | SEQ ID NO:11 + SEQ ID NO:12 | 60 | 63 |
| G | SEQ ID NO:13 + SEQ ID NO:14 | 63 | 60 |
| H | SEQ ID NO:15 + SEQ ID NO:16 | 60 | 60 |
| I | SEQ ID NO:17 + SEQ ID NO:18 | 55 | 53 |
| I | A + B + C | 170 | 175 |
| II | D + E + F | 186 | 186 |
| III | G + H + I | 178 | 173 | b) Cloning of the synthetic-gene-for human G-CSF

The synthetic gene, described above, was cloned into the plasmid vector, pSTP1 (Windass et al, Nucleic Acids Research (1983) Vol 10, p6639.

For vector preparation, 10 μg of STP1 was dissolved in water (37.5 μl) and 10×B restriction buffer (4.5 μl) (BCL). the restriction endonuclease SalI (3 μl) (BCL, 8 units/μl) was added and the mixture incubated at 37° C. for 1 hour until linearised plasmid was predominant over supercoiled and nicked circular forms. The DNA was precipitated with ethanol at 4° C. for 30 minutes, washed with ethanol:water (7:3) then dissolved in water (39.5 μl ), 10×H buffer (4.5 μl)(BCL). The restriction endonuclease EcoRI (1 μl) (BCL, 90 units/μl) was added and the mixture incubated at 37° C. for 1 hour until the large EcoRI-SalI fragment was predominant. The DNA was precipitated at −20° C. for 20 hours, washed with ethanol:water (7:3) then dissolved in water (20 μl)

The large EcoRI-SalI fragment was purified on a 1% preparative agarose gel and electroeluted and precipitated as described previously, then dissolved in water (20 μl). For ligation of the synthetic gene, a mixture of vector DNA (2 μl of the EcoRI-SalI fragment solution), synthetic gene (5 μl of the aqueous solution described previously, 5×ligase buffer (6 μl −250 mM Tris pH7.6 50 mM $MgCl_2$, 25% W/V PEG8000, 5MM ATP, 5 mM DTT exBRL) water (15 μl) and T4 DNA ligase (2 μl, 1 U/μl) was incubated at 16° C. for 4 hours. The DNA mix was used directly (either 1 μl of neat ligation mix or 2 μl of ligation mix diluted 5× with water) to transform E. coli strain HB101. The DNA mixture (1 or 2 μl) was added to competent E. coli HB101 cells (20 μl BR) on ice and the mixture incubated on ice for 45 min then heat shocked at 42° C. for 45 seconds. After 2 min on ice, 100 μl of SOC buffer (Bactotryptone 2%; Yeast Extract 0.5%; NaCl 10 mM; KCl 2.5 mm; $MgCl_2$, $MgSO_4$ 20 mm (10 mm each); glucose 20 mm) was added and the mixture incubated at 37° C. for 1 hour. aliquots of suspensions were plated onto L plates with 50 μl/ml ampicillin. transformants were screened for the presence of cloned synthetic gene by colony hybridisation analysis using standard methods described in "Molecular Cloning: A Laboratory Manual" by Maniatis et al (Cold Spring Harbor) and in UK Patent Application No 8502605. A total of 100 colonies were streaked onto filters (Schleicher and Schuell), grown at 37° C. for 20 hours, lysed and baked. The filter was hybridised at 65° C. for 20 hours with a radioactive probe prepared from oligonucleotide sequence SEQ ID No 1 by use of a random-label kit (Pharmacia). Five colonies 1–5 giving a positive hybridisation signal were grown up in L broth at 37° C. for 20 hours on a small scale (100 ml) and plasmid DNA prepared by centrifugation in a caesium chloride gradient essentially as described in "Molecular Cloning; A Laboratory Manual" by Maniatas et al (Cold Spring Harbor).

The DNA was sequenced by the standard dideoxy chain-termination method as described by Sanger et al in Proc. Nat. Acad Sci. USA 74, 5463–5467 (1977) using a Sequenase (Trade Mark) kit (United States Biochemical Corporation). Oligonucleotides SEQ ID NOS: 19 to 23 (as defined hereinafter and see Table 5) were used as sequencing primers.

TABLE 5

| CODE | PRIMING SITE |
|---|---|
| SEQ ID NO:19 | 214–234 top strand |
| SEQ ID NO:20 | 333–353 top strand |
| SEQ ID NO:21 | 375–395 bottom strand |
| SEQ ID NO:22 | 207–227 bottom strand |
| SEQ ID NO:23 | 69–93 bottom strand |

The plasmid DNA from clone 5 contained the DNA sequence shown in FIG. 6. The plasmid (pAG88) was used to transform competent cells of the following E.coli strains by standard procedures

HB101

CGSC 6300 (hereinafter also referred to as MSD 522)

The E. coli strains HB101 and MSD522 (CGSC 6300) are freely available. Thus for example they may be obtained from the E. coli Genetic Stock Centre, Yale University, USA. Moreover E. coli HB101 may additionally be obtained from for example BRL supplied by GIBCO Limited Unit 4, Cowley Mill Trading Estate, Longbridge Way, Uxbridge, UB8 2YG, Middlesex, England or GIBCO Laboratories, Life Technologies Inc., 3175 Staley Road, Grand Island, N. Y. 14072, USA.

c) Cloning of the gene for human G-CSF into an expression vector

The gene described above was cloned in the plasmid pICI 0020 as described in part (c) of the preparative route to pICI 1080 (described below) below to yield the expression plasmid pICI 1056.

PREPARATION OF pICI 1080

ROUTE 1

The procedure for steps a) and b) in the preparative route to pICI 1056 was repeated with the following modifications:

Oligonucleotides SEQ ID NOS: 24 to 27 (as hereinafter defined) replace SEQ ID NOS:1 to 4 (as hereinafter defined) respectively.

c) Cloning of the gene for [Ser $^{17,27}$] human G-CSF into an expression vector The gene described above (see FIGS. 7A–B and SEQ ID NO: 29) was cloned into plasmid vector pICI0020. This vector is a pAT153 based plasmid in which the 651 bp EcoRI-AccI region is replaced by a 167 bp EcoRI-ClaI fragment (SEQ ID NO:28) consisting of:

(1) a synthetic E. coli trp promoter and trp leader ribosome binding site (2) a translation initiation codon (3) a multiple restriction enzyme recognition sequence derived from M13mp18, containing sites for KpnI, BamHI, XbaI, SalI, PstI, SphI and HindIII (4) a synthetic transcription termination sequence The DNA sequence of this region is shown in FIG. 5. The pICI0020 expression vector was digested to completion with KpnI (BCL) in 10 mM Tris HCl (pH7.5), 10 mM magnesium chloride. The DNA was precipitated with ethanol at −20° C. from a solution containing 0.3M sodium acetate and then the 3'- sticky ends were removed by treatment with T4 DNA polymerase for 10 minutes at 37° C. as follows:

DNA (1 μg) in water (16 μl)
10×T4 polymerase buffer (2 μl)
0.33M Tris acetate pH7.9
0.1M Magnesium acetate
0.66M Potassium acetate
5 mM dithiothreitol
1 mg/ml bovine serum albumin (BSA PENTAX fraction V)
2 mM dNTP mixture (1 μl)
T4 DNA polymerase (1 μl; 2.5 units/μl BCL)

Water (80 μl) was added and the mixture extracted with phenol/chloroform (100 μl) and then with chloroform (100 μl). The DNA was precipitated with ethanol (250 μl) at −20° C. after addition of 3M sodium acetate (10 μl) then digested to completion with SalI (BCL) in 150 mM NaCl, 10 mM MgCl$_2$ and 10 mM Tris HCl (pH7.5). The Kpn-blunt ended to SalI vector was purified from a 0.7% agarose gel and isolated by use of "GENECLEAN" (trademark) following the manufacturer's (Bio101, USA) recommended procedure.

The synthetic gene was isolated from the pSTP1 vectors as follows. The vectors were digested with ScaI and SalI (both from BCL) in 100 mM Nacl, 10 mM MgCl$_2$ and 10 mM Tris HCl (pH7.5). The 530 bp fragment was purified from a 0.7% agarose gel and isolated by use of "GENECLEAN" (trademark) following the manufacturer's (Bio101) recommended procedure.

For ligation, a mixture of the ScaI-SalI gene fragment (50ng) and the pICI0020 vector fragment (100 ng) in 20 μl of a solution containing 50 mM Tris HCl (pH7.6), 10 mM MgCl$_2$, 1 mM ATP, 1 mM DTT, 5% w/v PEG 8000 and T4 DNA ligase (2 units; BRL) were incubated at 16° C. for 20 hours. The resulting mixture was used to transform competent E. coli HB101 cells (as supplied by BRL) as described herein. Transformants were selected for by growth on L-agar plates containing 50 μg/ml ampicillin and screened for the presence of the gene by colony hybridisation with a $^{32}$P labelled probe (SEQ ID NO: 24) as described herein. Plasmid DNA was prepared from 6 positively hybridising colonies, purified by centrifugation in a caesium chloride gradient and the sequence confirmed by dideoxy sequencing as described herein.

The plasmid containing this gene was designated pICI 1080.

ROUTE 2

The procedure described in route 1 was repeated except as follows:

The duplex I was phosphorylated with T4 polynucleotide kinase and digested with MstII (10 units) in 1×H buffer (BCL; 30 μl) for 2 hours at 37° C.

Following precipitation with ethanol, the 143 bp EcoRI-MstII fragment was purified on a 10% polyacrylamide gel containing 7M urea, isolated by electroelution from a gel slice and the DNA strands annealed as described in the preparation of pICI1056.

The synthetic EcoRI-MstII fragment described above was cloned into the plasmid vector pAG88 described in Reference Example 1. For vector preparation, pAG88 (10 μg) was digested with MstII (20 units; BCL) in 1×H buffer (BCL; 100 μl) for 2 hours at 37° C. The DNA was precipitated with ethanol from 0.3M sodium acetate at −20° C. then digested with EcoRI (20 units; BCL) in 1×H buffer (BCL; 100 μl) for 2 hours at 37° C. Following precipitation with ethanol, the large EcoRI-MstII fragment was purified on a 1% agarose gel and purified using "GENECLEAN" (trademark) as described by the manufacturer (Bio 101, USA). Colonies containing the synthetic fragment were confirmed by screening with a radioactive probe prepared from oligonucleotide (SEQ ID NO: 24) and the correct sequence confirmed by DNA sequencing as described in the preparation of pICI1056. The plasmid containing the gene for [Ser$^{17,27}$]G-CSF was designated pICI1107. The gene was cloned into expression vector pICI0020 to give p1080.

PREPARATION OF pICI 1197

The preparation of pICI 1197 is illustrated in FIGS. 10, 11A–B, 12.

Many plasmid vectors are based on one of the original cloning vectors: pBR322 (Bolivar et al, 1977., Gene 2: 95–113). The non-mobilizable pAT153 is a derivative of this (Twigg and Sherratt, 1980, Nature 283: 216–218). Both these plasmids contain the ampicillin resistance determinant, TEM β-lactamase.

Plasmid pICI 1197 utilises a repressed tetracycline resistance determinant, as found on the naturally-occurring plasmid RP4. This repressed system shuts off expression of the tetA gene in the absence of tetracycline whereas most drug resistant mechanisms have constitutive expression.

The tet locus was first mapped on RP4 by Barth and Grinter (J.Mol. Biol.113: 455–474, 1977). This was shown to consist of adjacent genes: tetA, the structural resistance gene and tetR, the repressor gene and this region has been sequenced (Klock et al, J. Bacteriol: 161:326–332, 1985). These genes are located on adjacent BglII-SmaI and SmaI-SmaI fragments. The BglII site is unique in RP4 but there are five SmaI sites (Lanka, Lurz and Furste, Plasmid 10: 303–307, 1983).

Cloning the tetA+tetR genes

The plasmid RP4 is well documented (Datta et al, J. Bacteriol 108: 1244, 1971) and is freely available. RP4 obtained from N Datta was used herein. E. coli strains containing this-plasmid were grown in selective broth cultures and plasmid DNA was isolated by a scale-up of the Holmes and Quigley method (Holmes and Quigley, Anal. Biochem 114: 193–197, 1981). It was deproteinized by treatment with 2.5M ammonium acetate and reprecipitated with isopropanol. This plasmid DNA was treated, according to the supplier's recommended conditions, with restriction enzyme BglII and cut to completion. It was then partially cut by XmaI by using diluted enzyme and short incubation times. XmaI is an isoschizomer of SmaI but which produces 4-nucleotide cohesive ends at its cut sites.

The vector plasmid pUC8 (Yanisch-Perron, Vieira and Messing, Gene 33: 103–119, 1985) was similarly prepared and cut with BamHI and XmaI to completion. The RP4 fragments were cloned into this vector by ligation with T4 ligase at 12° C. for 16 hours. This was used to transform E. coli C600 made competent by the calcium chloride method (Maniatis et al, Cold Spring Harbor Laboratory, 1982). Cultures were then plated onto medium which selected for tetracycline resistance.

Several colonies with this resistance were checked for the expected phenotype (ampicillin and tetracycline resistance but not the kanamycin resistance indicative of RP4 itself).

Colonies with the correct resistances were subjected to clone analysis by isolating plasmid DNA (Holmes-and Quigley method). These preparations were cut with EcoRI and HindIII and analysed by gel electrophoresis. This established the size of the cloned insert which was found to be the 2.45 kb predicted for the BglII-XmaI-XmaI fragment from RP4. A clone carrying this fragment containing the tetA and tetR genes was designated pTB344.

Removal of the tet gene from pAT153

It was necessary to remove the tet gene from the vector plasmid pAT153 before inserting the tetA+tetR cassette from RP4 to prevent gene duplication which can be a source of genetic instability. Also the tet gene may not be effectively suppressed by the non-cognate tetR. The removal was done by isolating plasmid pAT153 DNA and cutting it with EcoRI and AvaI. Between these sites, synthetic oligonucleotides with the sequence:

5' AATTCGCATGCGGATCCATCGATC 3' (SEQ ID NO:32)

3' GCGTACGCCTAGGTAGCTAGAGCC 5' (SEQ ID NO:33) were cloned. These fit the EcoRI and AvaI cohesive ends and contain SphI, BamHI and ClaI sites in addition. After transformation and selection, colonies were tested for the loss of the tetracycline resistance determinant. Plasmid DNA from one clone was sequenced to confirm that the predicted sequence was correct. This plasmid was designated pCH19.

Insertion of the tetA+tetR genes

The tetA and tetR genes were isolated from pTB344 on an EcoRI to PstI fragment. The pUC8 vector was destroyed by cutting with SspI because it carries the same selection determinant (ampicillin resistance) as pCH19. Plasmid pCH19 DNA was cut with EcoRI and PstI and then ligated with the 2.45 kb fragment carrying the tet genes. This was used to transform *E.coli* C600, the culture being plated out under selection for tetracycline resistant colonies. The insertion of the tet genes was designed to replace most of the bla gene in pCH19 which should thus lose its ampicillin resistance determinant. Loss of ampicillin resistance from the transformants was confirmed. A few clones were then used to isolate plasmid DNA which was subjected to restriction analysis. This confirmed that the constructed plasmid had the intended structure. It was designated pTB351.

Insertion of the cer sequence

The naturally-occurring plasmid ColEI is very stably maintained in *E.coli*, whereas its derivatives pBR322 and pAT153 are not. Summers and Sherratt (*Cell*, 36: 1097–1103, 1984) demonstrated that this was due to the derivatives not containing a short (283 bp) sequence called cer which is present in the parent plasmid. This sequence contains a site-specific plasmid multimer-resolution system which prevents the accumulation of plasmid multimers formed by homologous recombination. Such multimers have a deleterious effect on the process of partition which normally ensures stable inheritance of daughter plasmids during bacterial cell division.

Figure 10:
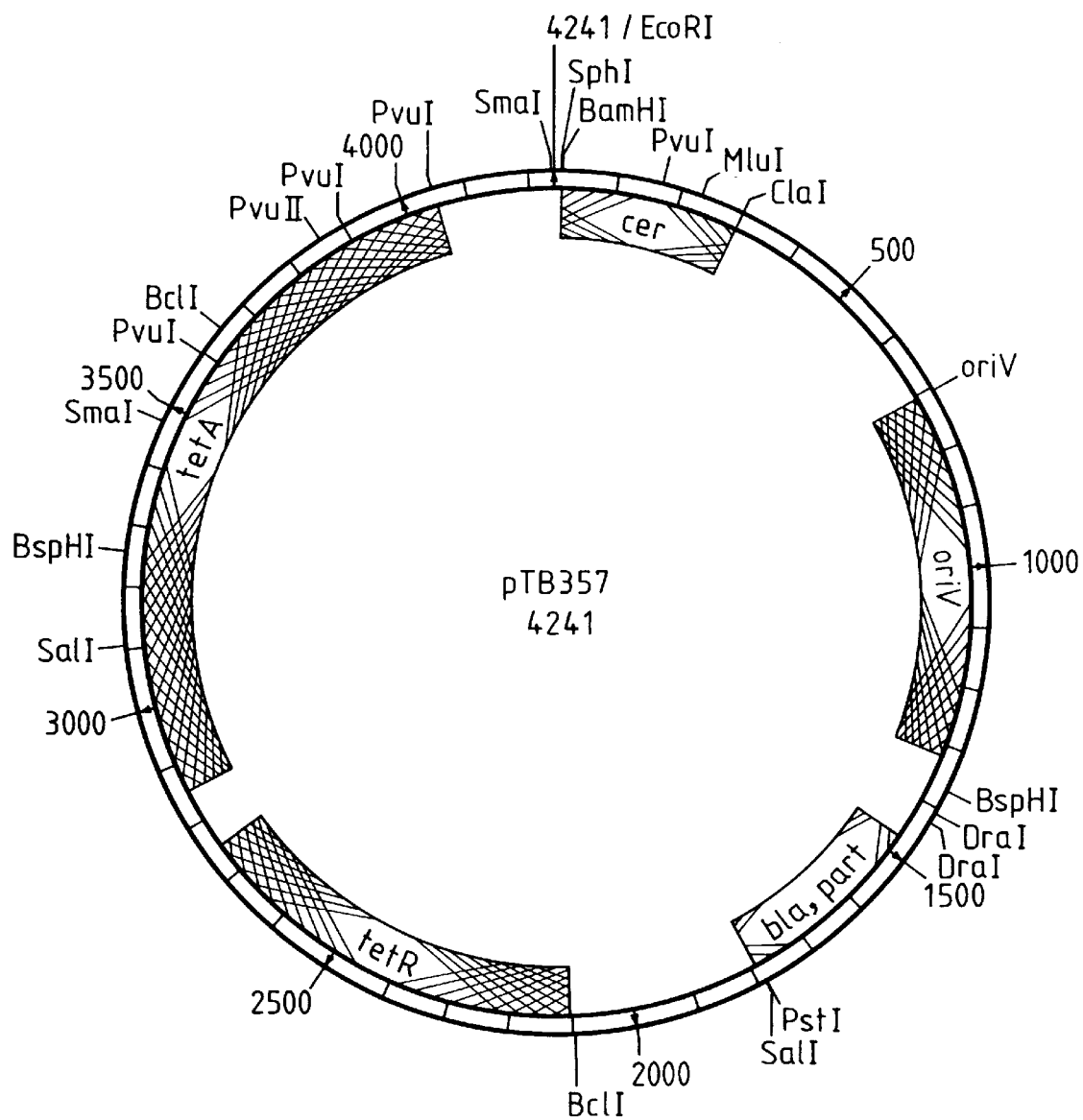
FIG. 10 shows plasmid pTB357.
Figure 11A:
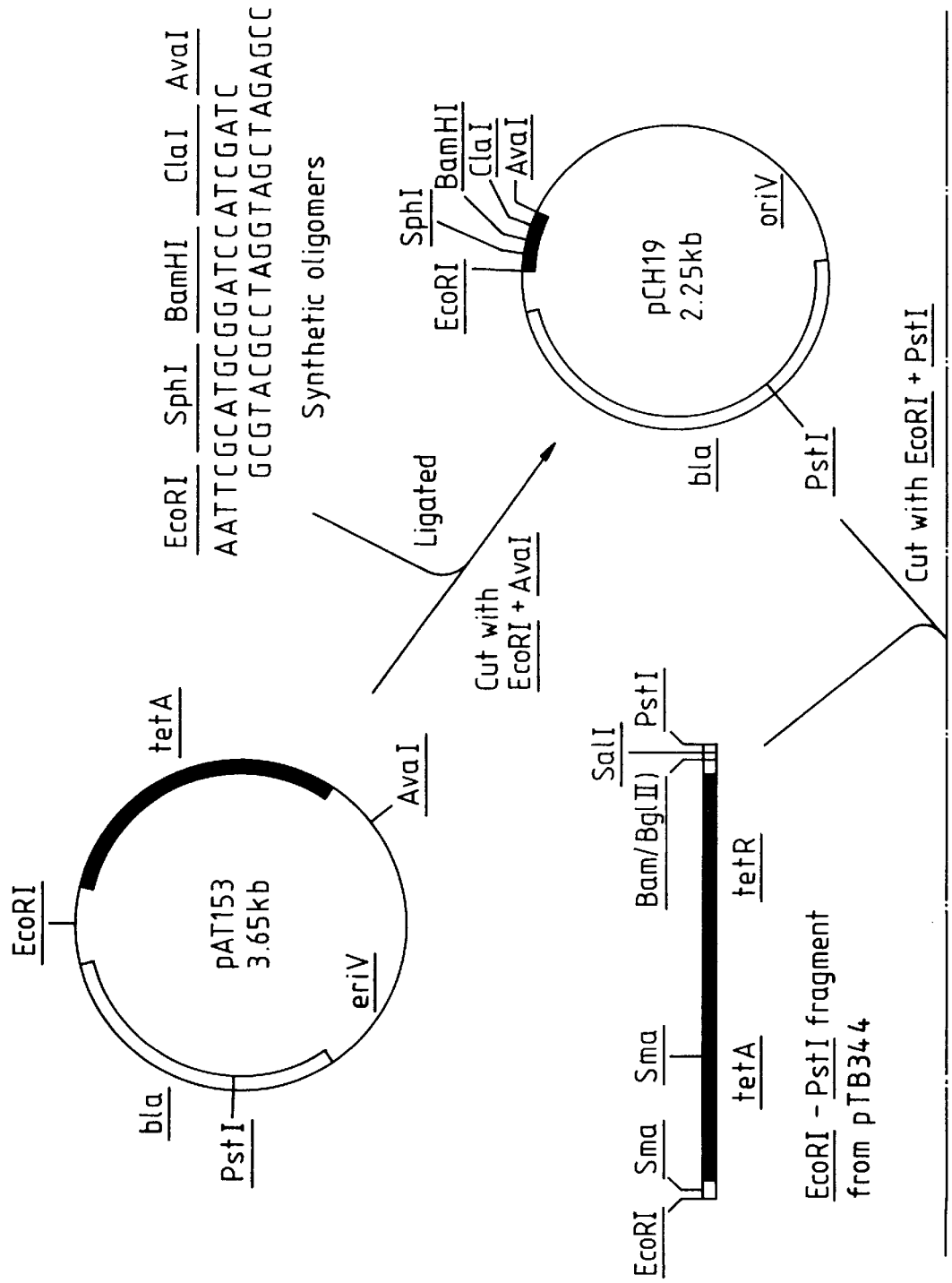
FIGS. 11A–11B show construction of pTB357. The synthetic oligomers are SEQ ID NOS:32 and 33.
Figure 11B:
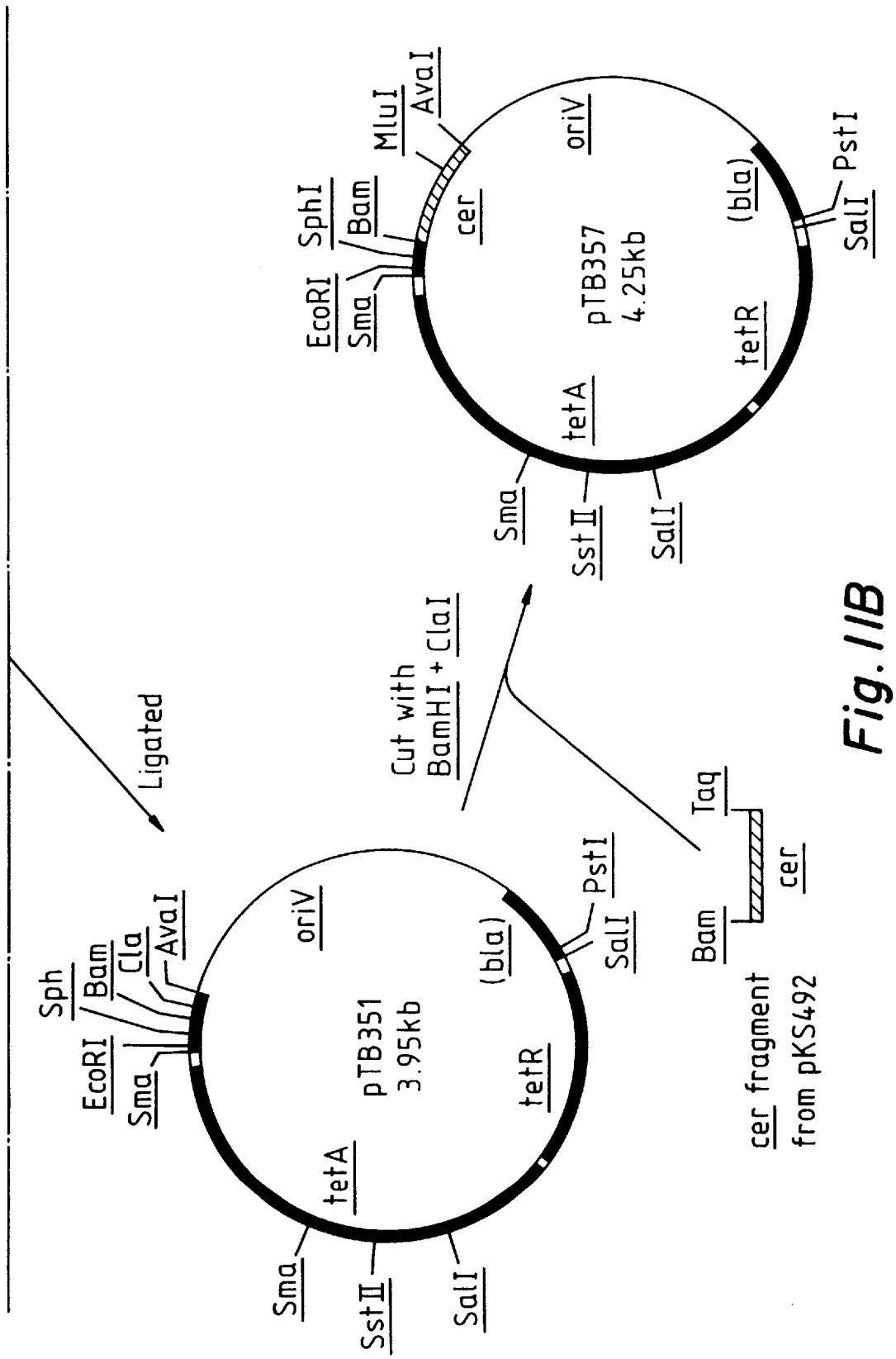
Figure 12:
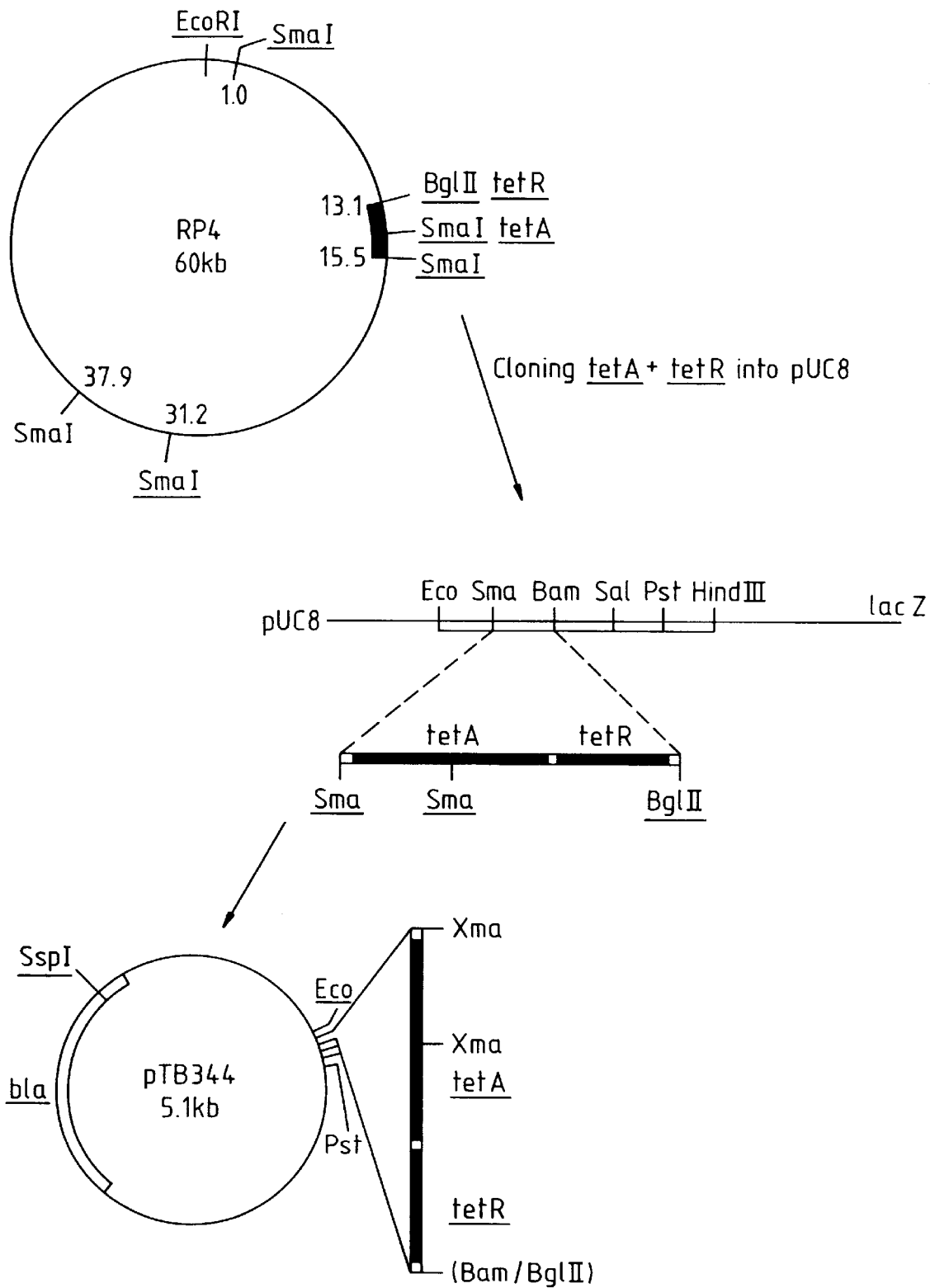
FIG. 12 shows cloning the tetA and tetR genes to produce pTB344.

The cer sequence (Summers, D. et al MGG, 201, p334–338, 1985) was isolated from plasmid pKS492 (provided by D. Sherratt) as a 289 bp fragment by cutting with BamHI and TaqI. The plasmid pTB351 was isolated as DNA from a dam strain of *E. coli* to prevent its ClaI site being blocked by the dam$^+$ methylation system. This DNA was cut with BamHI and ClaI (both these sites having been introduced on the synthetic oligonucleotide for this cloning). The cer fragment was ligated with the cut vector and then used to transform *E. coli* C600, selection being made for tetracycline reisistance. Transformant colonies were subjected to clone analysis by AvaI restriction and gel electrophoresis. The presence of an extra DNA band of about 300 bp indicated the acquisition of the cer fragment. Further restriction analyses were used to confirm that resultant plasmids had the correct structure. One of these was designated pTB357 (FIG. 10).

Preparation of pAG52

An expression cassette containing a trp promoter sequence and a gene for [Ser $^{17,27}$] human G-CSF was isolated from plasmid pICI1080 (preparation described above) as follows:

A mixture of plasmid DNA (20 μg), EcoRI (90 units; BCL) and SalI (35 units; BCL) in water (100 μl) containing 50 mM Tris HCl (pH 7.5), 10 mM MgCl$_2$, 100 mM NaCl and 1 mM dithioerythritol were incubated at 37° C. for 1 hour. The small EcoRI-SalI fragment was purified by electrophoresis on a 1% agarose gel and isolated from the gel by first electroeluting the DNA onto DEAE NA45 paper then eluting the DNA from the NA45 paper with IM NaCl solution. This procedure is described in EP 402,068 (see in particular p 18).

For vector preparation, pICI1079 * was digested as described above with EcoRI and SalI and the large EcoRI-SalI fragment isolated from a 1% agarose gel by electroelution onto NA45 paper. DNA samples of the expression cassette and vector were precipitated with ethanol (1 ml) at 4° C. for 10 minutes. The DNA was collected by centrifugation, washed with ethanol:water (7:3), dried and dissolved in water. The fragments-were ligated and the ligation mix used to transform competent *E. Coli* strain HB101 as described above in the preparation of pICI 1080. Plasmids containing the gene were identified and isolated as described above in the preparation of pICI 1080 and designated pAG52.

Figure 9:
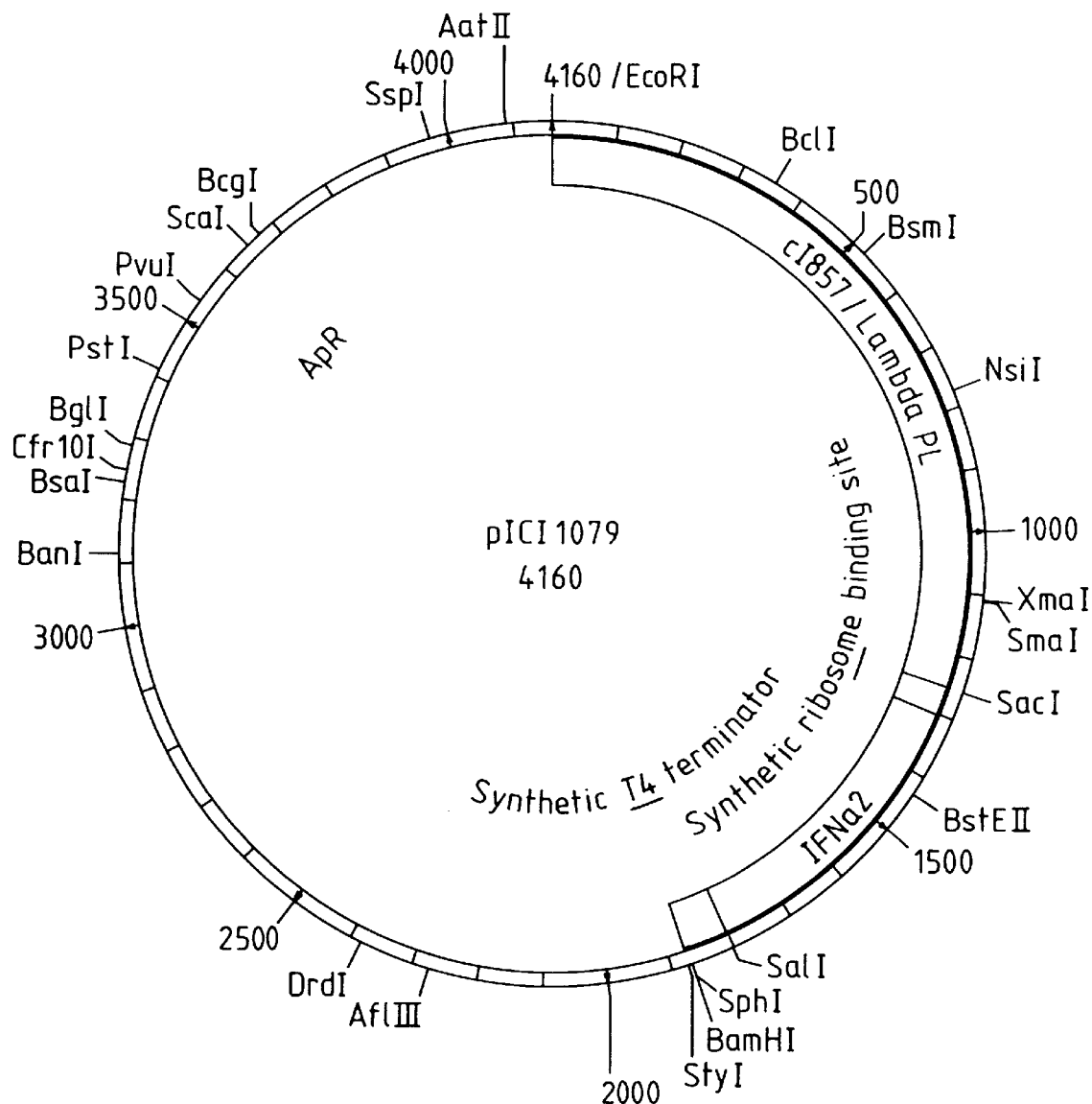
FIG. 9 shows plasmid pICI1079.

NOTE pICI1079 is an ampicillin resistant, pAT153-derived plasmid containing the following elements between the EcoRI and StyI restriction sites:

(i) a CI857 gene from phage λ;

(ii) a λP$_L$ promoter;

(iii) a synthetic ribosome binding site;

(iv) a synthetic interferon α2 gene sequence;

(v) a synthetic transcription terminator sequence, derived from phage T4, between the SalI and StyI restriction sites. The DNA sequence of this transcription terminator is shown in FIG. 8 and SEQ ID NOS: 34 and 35 pICI1079 is illustrated in FIG. 9.

pICI1079 has been deposited under the Budapest Treaty, at the National Collections of Industrial and Marine Bacteria Limited (NCIMB), 23 St. Machar Drive, Aberdeen, AB2 1RY, Scotland, UK. (NCIMB No 40370, date of deposit 19 February 1991).

Preparation of pICI1197

An expression cassette containing a trp promoter, a gene for [Ser $^{17,27}$] human G-CSF and a T4 transcription terminator was isolated from plasmid pAG52 (10 μg) as described above with SalI replaced by SphI (16 units, BCL) and in a total volume of 120 μl . The small EcoI-SphI fragment was purified as described above and dissolved in water.

Vector DNA was prepared in a similar manner from pTB357 (10 μg) by digestion with EcoRI and SphI (24 units) in a total volume of 50 μl and the large EcoRI-SphI fragment purified by precipitation with ethanol at −20° C. from a solution containing 0.3M sodium acetate, washed with ethanol:water (7.3), dried and dissolved in water.

The expression cassette and vector were ligated as described in the preparation of pICI1080 (above) and the resulting mixture was used to transform competent *E. coli* HB101 cells. Transformants were selected for by growth on L-agar plates containing 15 μg/ml tetracycline and screened for the presence of the [Ser$^{17,27}$] human G-CSF gene as follows:

24 colonies were separately added to 10 ml L-broth containing tetracycline (15 μg/ml). After growth for 16 h at 37° C. on a reciprocating shaker, plasmid DNA was isolated from each by the method of Birnboim and Doly as described in "Molecular cloning—a laboratory manual" Sambrook, Fritsch and Maniatis (Cold Spring Harbor Publication).

Plasmid DNA samples were digested with XbaI (8 Units; BCL) in water (30 μl) containing 50 mM Tris HCl (pH7.5), 10 mM MgCl$_2$, 100 mM NaCl and 1 mM dithioerythritol at 37° C. for 2 h. Two samples (clones 18 and 20) cut with XbaI (as indicated by electrophoresis of the samples on an agarose gel). The plasmid DNA from clone 18 was designated pICI1197 and was used to transform *E.coli* strain MSD522 (CGSC 6300).

CGSC 6300 is freely available, and may be obtained, for example, from the Genetic Stock Centre, Yale University, USA.

We claim:

1. A process for expressing a polypeptide, said process comprising cultivating a bacterial host cell transformed with a vector or plasmid carrying genetic material coding for said polypeptide in the presence of at least one amino acid which is present in an amount sufficient to inhibit growth of the host cell and thereby accumulate the polypeptide, and in which the host cell is not auxotrophic for said amino acid.

2. A process for expressing a polypeptide, said process comprising cultivating a bacterial host cell transformed with a vector or plasmid carrying genetic material coding for said polypeptide in the presence of a growth medium and adding to the growth medium a supplement comprising at least one amino acid so that the amino acid is present in the growth medium in an amount sufficient to inhibit growth of the host cell and thereby accumulate the polypeptide.

3. The process according to claim 2 wherein the host cell is not auxotrophic for said amino acid.

4. The process according to claim 1 or 3 wherein the amino acid is leucine or threonine.

5. The process according to claim 4 wherein the leucine or threonine is present in a concentration in the range of about 0.625 to about 5 g/l.

6. The process according to claim 5 wherein the amino acid is leucine.

7. The process according to claim 6 wherein the concentration of leucine is about 2.5 g/l.

8. The process according to claim 6 wherein the concentration of leucine is about 0.625 g/l.

9. The process according to claim 1 or 3 wherein the amino acid is leucine and threonine.

10. The process according to claim 1 or 2 wherein said polypeptide is human granulocyte colony stimulating factor (human G-CSF) or an analogue thereof.

11. The process according to claim 10 wherein said genetic material coding for human G-CSF or an analogue thereof is operably linked to a trp promoter.

12. The process according to claim 1 or 2 in which a substance which stimulates growth of the host cell is present.

13. The process according to claim 12 wherein said substance comprises casein hydrolysate or isoleucine.

14. The process according to claim 1 in which the host cell is an *E. coli* cell.

15. A process for expressing a polypeptide, said process comprising cultivating a host cell, wherein the host cell is an

*E. coli* host cell which is a prototroph and which is transformed with a vector or plasmid carrying genetic material coding for said polypeptide, in the presence of an amount of leucine or threonine sufficient to inhibit growth of the host cell and thereby accumulate the polypeptide.

16. The process according to claim 15 wherein the leucine or threonine is present in a concentration in the range of about 0.625 to about 5 g/l.

17. A process for expressing a polypeptide, said process comprising cultivating a host cell, wherein the host cell is an *E. coli* host cell which is a prototroph and which is transformed with a vector or plasmid carrying genetic material coding for said polypeptide, in the presence of an amount of leucine and threonine sufficient to inhibit growth of the host cell and thereby accumulate the polypeptide.

18. The process according to claim 1 wherein said amino acid is selected from the group consisting of leucine and threonine, said cultivating being carried out at a temperature of about 37° C. and at a pH of about 6.8 and said genetic material coding for said polypeptide being operably linked to a trp promoter.

* * * * *

SEQUENCE LISTING ( 1 ) GENERAL INFORMATION:

( i i i ) NUMBER OF SEQUENCES: 35

( 2 ) INFORMATION FOR SEQ ID NO:1:

( i ) SEQUENCE CHARACTERISTICS:
  ( A ) LENGTH: 62 base pairs
  ( B ) TYPE: nucleic acid
  ( C ) STRANDEDNESS: single
  ( D ) TOPOLOGY: linear ( x i ) SEQUENCE DESCRIPTION: SEQ ID NO:1:

```
AATTCAGTAC  TCCACTGGGT  CCAGCAAGCT  CTCTGCCGCA  GTCTTTCCTG  CTGAAGTGTC      60
TC                                                                          62
```

( 2 ) INFORMATION FOR SEQ ID NO:2:

( i ) SEQUENCE CHARACTERISTICS:
  ( A ) LENGTH: 64 base pairs
  ( B ) TYPE: nucleic acid
  ( C ) STRANDEDNESS: single
  ( D ) TOPOLOGY: linear ( x i ) SEQUENCE DESCRIPTION: SEQ ID NO:2:

```
CTGTTCGAGA  CACTTCAGCA  GGAAAGACTG  CGGCAGAGAG  CTTGCTGGAC  CCAGTGGAGT      60
ACTG                                                                        64
```

( 2 ) INFORMATION FOR SEQ ID NO:3:

( i ) SEQUENCE CHARACTERISTICS:
  ( A ) LENGTH: 60 base pairs
  ( B ) TYPE: nucleic acid
  ( C ) STRANDEDNESS: single
  ( D ) TOPOLOGY: linear ( x i ) SEQUENCE DESCRIPTION: SEQ ID NO:3:

```
GAACAGGTAC  GTAAAATTCA  AGGCGATGGT  GCGGCTCTGC  AGGAAAAGCT  GTGCGCAACC      60
```

( 2 ) INFORMATION FOR SEQ ID NO:4:

( i ) SEQUENCE CHARACTERISTICS:
  ( A ) LENGTH: 60 base pairs
  ( B ) TYPE: nucleic acid
  ( C ) STRANDEDNESS: single
  ( D ) TOPOLOGY: linear ( x i ) SEQUENCE DESCRIPTION: SEQ ID NO:4:

```
TTTGTAGGTT  GCGCACAGCT  TTTCCTGCAG  AGCCGCACCA  TCGCCTTGAA  TTTTACGTAC      60
```

( 2 ) INFORMATION FOR SEQ ID NO:5:

( i ) SEQUENCE CHARACTERISTICS:
  ( A ) LENGTH: 48 base pairs
  ( B ) TYPE: nucleic acid
  ( C ) STRANDEDNESS: single
  ( D ) TOPOLOGY: linear ( x i ) SEQUENCE DESCRIPTION: SEQ ID NO:5:

TACAAACTGT GCCACCCTGA GGAACTGGTG CTGCTCGGTC ACTCTCTG    48

( 2 ) INFORMATION FOR SEQ ID NO:6:

( i ) SEQUENCE CHARACTERISTICS:
    ( A ) LENGTH: 51 base pairs
    ( B ) TYPE: nucleic acid
    ( C ) STRANDEDNESS: single
    ( D ) TOPOLOGY: linear ( x i ) SEQUENCE DESCRIPTION: SEQ ID NO:6:

CGGGATCCCC AGAGAGTGAC CGAGCAGCAC CAGTTCCTCA GGGTGGCACA G    51

( 2 ) INFORMATION FOR SEQ ID NO:7:

( i ) SEQUENCE CHARACTERISTICS:
    ( A ) LENGTH: 63 base pairs
    ( B ) TYPE: nucleic acid
    ( C ) STRANDEDNESS: single
    ( D ) TOPOLOGY: linear ( x i ) SEQUENCE DESCRIPTION: SEQ ID NO:7:

GGGATCCCGT GGGCTCCACT GAGCTCTTGC CCGTCCCAAG CTTTACAACT GGCAGGCTGC    60

TTG    63

( 2 ) INFORMATION FOR SEQ ID NO:8:

( i ) SEQUENCE CHARACTERISTICS:
    ( A ) LENGTH: 60 base pairs
    ( B ) TYPE: nucleic acid
    ( C ) STRANDEDNESS: single
    ( D ) TOPOLOGY: linear ( x i ) SEQUENCE DESCRIPTION: SEQ ID NO:8:

CTGGCTCAAG CAGCCTGCCA GTTGTAAAGC TTGGGACGGG CAAGAGCTCA GTGGAGCCCA    60

( 2 ) INFORMATION FOR SEQ ID NO:9:

( i ) SEQUENCE CHARACTERISTICS:
    ( A ) LENGTH: 63 base pairs
    ( B ) TYPE: nucleic acid
    ( C ) STRANDEDNESS: single
    ( D ) TOPOLOGY: linear ( x i ) SEQUENCE DESCRIPTION: SEQ ID NO:9:

AGCCAGCTGC ACTCCGGTCT GTTCCTGTAC CAGGGTCTGC TGCAGGCTCT AGAAGGCATC    60

TCT    63

( 2 ) INFORMATION FOR SEQ ID NO:10:

( i ) SEQUENCE CHARACTERISTICS:
    ( A ) LENGTH: 63 base pairs
    ( B ) TYPE: nucleic acid
    ( C ) STRANDEDNESS: single
    ( D ) TOPOLOGY: linear ( x i ) SEQUENCE DESCRIPTION: SEQ ID NO:10:

TTCAGGAGAG ATGCCTTCTA GAGCCTGCAG CAGACCCTGG TACAGGAACA GACCGGAGTG    60

CAG                                                                                                                                    63

( 2 ) INFORMATION FOR SEQ ID NO:11:

( i ) SEQUENCE CHARACTERISTICS:
        ( A ) LENGTH: 60 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:11:

CCTGAATTGG GGCCCACCCT GGACACACTG CAGCTGGACG TTGCCGACTT CGCTACTACC    60

( 2 ) INFORMATION FOR SEQ ID NO:12:

( i ) SEQUENCE CHARACTERISTICS:
        ( A ) LENGTH: 63 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:12:

TTGCCATATG GTAGTAGCGA AGTCGGCAAC GTCCAGCTGC AGTGTGTCCA GGGTGGGCCC    60

CAA                                                                                                                                    63

( 2 ) INFORMATION FOR SEQ ID NO:13:

( i ) SEQUENCE CHARACTERISTICS:
        ( A ) LENGTH: 63 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:13:

ATATGGCAAC AGATGGAGGA ACTGGGTATG GCTCCGGCAC TGCAGCCGAC TCAGGGTGCG    60

ATG                                                                                                                                    63

( 2 ) INFORMATION FOR SEQ ID NO:14:

( i ) SEQUENCE CHARACTERISTICS:
        ( A ) LENGTH: 60 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:14:

TGCTGGCATC GCACCCTGAG TCGGCTGCAG TGCCGGAGCC ATACCCAGTT CCTCCATCTG    60

( 2 ) INFORMATION FOR SEQ ID NO:15:

( i ) SEQUENCE CHARACTERISTICS:
        ( A ) LENGTH: 60 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:15:

CCAGCATTCG CCTCTGCTTT CCAGCGGCGC GCAGGCGGTG TTCTGGTTGC CTCCATCTT    60

( 2 ) INFORMATION FOR SEQ ID NO:16:

( i ) SEQUENCE CHARACTERISTICS:
        ( A ) LENGTH: 60 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:16:

GCTCTGAAGA TGGGAGGCAA CCAGAACACC GCCTGCGCGC CGCTGGAAAG CAGAGGCGAA    60

( 2 ) INFORMATION FOR SEQ ID NO:17:

( i ) SEQUENCE CHARACTERISTICS:
        ( A ) LENGTH: 55 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:17:

CAGAGCTTCC TCGAGGTGTC TTACCGCGTT CTGCGTCACC TGGCCCAGCC GTTAG    55

( 2 ) INFORMATION FOR SEQ ID NO:18:

( i ) SEQUENCE CHARACTERISTICS:
        ( A ) LENGTH: 53 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:18:

TCGACTTACG GCTGGGCCAG GTGACGCAGA ACGCGGTAAG ACACCTCGAG GAA    53

( 2 ) INFORMATION FOR SEQ ID NO:19:

( i ) SEQUENCE CHARACTERISTICS:
        ( A ) LENGTH: 21 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:19:

TACAACTGGC AGGCTGCTTG A    21

( 2 ) INFORMATION FOR SEQ ID NO:20:

( i ) SEQUENCE CHARACTERISTICS:
        ( A ) LENGTH: 21 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:20:

GACGTTGCCG ACTTCGCTAC T    21

( 2 ) INFORMATION FOR SEQ ID NO:21:

( i ) SEQUENCE CHARACTERISTICS:
        ( A ) LENGTH: 21 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:21:

TGCCGGAGCC ATACCCAGTT C    21

( 2 ) INFORMATION FOR SEQ ID NO:22:

( i ) SEQUENCE CHARACTERISTICS:
        ( A ) LENGTH: 21 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:22:

GCCTGCCAGT TGTAAAGCTT G                                                                                     21

( 2 ) INFORMATION FOR SEQ ID NO:23:

( i ) SEQUENCE CHARACTERISTICS:
        ( A ) LENGTH: 26 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:23:

GCACCATCGC CTTGAATTTT ACGTAG                                                                                26

( 2 ) INFORMATION FOR SEQ ID NO:24:

( i ) SEQUENCE CHARACTERISTICS:
        ( A ) LENGTH: 62 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:24:

AATTCAGTAC TCCACTGGGT CCAGCAAGCT CTCTGCCGCA GTCTTTCCTG CTGAAGTCTC                                            60

TC                                                                                                          62

( 2 ) INFORMATION FOR SEQ ID NO:25:

( i ) SEQUENCE CHARACTERISTICS:
        ( A ) LENGTH: 64 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:25:

CTGTTCGAGA GACTTCAGCA GGAAAGACTG CGGCAGAGAG CTTGCTGGAC CCAGTGGAGT                                            60

ACTG                                                                                                        64

( 2 ) INFORMATION FOR SEQ ID NO:26:

( i ) SEQUENCE CHARACTERISTICS:
        ( A ) LENGTH: 60 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:26:

GAACAGGTAC GTAAAATTCA AGGCAGCGGT GCGGCTCTGC AGGAAAAGCT GTGCGCAACC                                            60

( 2 ) INFORMATION FOR SEQ ID NO:27:

( i ) SEQUENCE CHARACTERISTICS:
        ( A ) LENGTH: 60 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:27:

TTTGTAGGTT GCGCACAGCT TTTCCTGCAG AGCCGCACCG CTGCCTTGAA TTTTACGTAC                                            60

( 2 ) INFORMATION FOR SEQ ID NO:28:

( i ) SEQUENCE CHARACTERISTICS:
        ( A ) LENGTH: 172 base pairs
        ( B ) TYPE: nucleic acid
        ( C ) STRANDEDNESS: single
        ( D ) TOPOLOGY: linear (xi) SEQUENCE DESCRIPTION: SEQ ID NO:28:

```
AATTCTGGCA AATATTCTGA AATGAGCTGT TGACAATTAA TCATCGAACT AGTTAACTAG      60
TACGCAAGTT CACGTAAAAA GGGTATCGAC AATGGTACCC GGGGATCCTC TAGAGTCGAC     120
CTGCAGGCAT GCAAGCTTAG CCCGCCTAAT GAGCGGGCTT TTTTTATCG AC              172
```

(2) INFORMATION FOR SEQ ID NO:29:

(i) SEQUENCE CHARACTERISTICS:
        (A) LENGTH: 534 base pairs
        (B) TYPE: nucleic acid
        (C) STRANDEDNESS: single
        (D) TOPOLOGY: linear (ix) FEATURE:
        (A) NAME/KEY: CDS
        (B) LOCATION: 9..530

(xi) SEQUENCE DESCRIPTION: SEQ ID NO:29:

```
AATTCAGT ACT CCA CTG GGT CCA GCA AGC TCT CTG CCG CAG TCT TTC CTG       50
         Thr Pro Leu Gly Pro Ala Ser Ser Leu Pro Gln Ser Phe Leu
         1               5                   10

CTG AAG TCT CTC GAA CAG GTA CGT AAA ATT CAA GGC AGC GGT GCG GCT        98
Leu Lys Ser Leu Glu Gln Val Arg Lys Ile Gln Gly Ser Gly Ala Ala
15              20                  25                  30

CTG CAG GAA AAG CTG TGC GCA ACC TAC AAA CTG TGC CAC CCT GAG GAA       146
Leu Gln Glu Lys Leu Cys Ala Thr Tyr Lys Leu Cys His Pro Glu Glu
                35                  40                  45

CTG GTG CTG CTC GGT CAC TCT CTG GGG ATC CCG TGG GCT CCA CTG AGC       194
Leu Val Leu Leu Gly His Ser Leu Gly Ile Pro Trp Ala Pro Leu Ser
            50                  55                  60

TCT TGC CCG TCC CAA GCT TTA CAA CTG GCA GGC TGC TTG AGC CAG CTG       242
Ser Cys Pro Ser Gln Ala Leu Gln Leu Ala Gly Cys Leu Ser Gln Leu
        65                  70                  75

CAC TCC GGT CTG TTC CTG TAC CAG GGT CTG CTG CAG GCT CTA GAA GGC       290
His Ser Gly Leu Phe Leu Tyr Gln Gly Leu Leu Gln Ala Leu Glu Gly
    80                  85                  90

ATC TCT CCT GAA TTG GGG CCC ACC CTG GAC ACA CTG CAG CTG GAC GTT       338
Ile Ser Pro Glu Leu Gly Pro Thr Leu Asp Thr Leu Gln Leu Asp Val
95                  100                 105                 110

GCC GAC TTC GCT ACT ACC ATA TGG CAA CAG ATG GAG GAA CTG GGT ATG       386
Ala Asp Phe Ala Thr Thr Ile Trp Gln Gln Met Glu Glu Leu Gly Met
                115                 120                 125

GCT CCG GCA CTG CAG CCG ACT CAG GGT GCG ATG CCA GCA TTC GCC TCT       434
Ala Pro Ala Leu Gln Pro Thr Gln Gly Ala Met Pro Ala Phe Ala Ser
            130                 135                 140

GCT TTC CAG CGG CGC GCA GGC GGT GTT CTG GTT GCC TCC CAT CTT CAG       482
Ala Phe Gln Arg Arg Ala Gly Gly Val Leu Val Ala Ser His Leu Gln
        145                 150                 155

AGC TTC CTC GAG GTG TCT TAC CGC GTT CTG CGT CAC CTG GCC CAG CCG       530
Ser Phe Leu Glu Val Ser Tyr Arg Val Leu Arg His Leu Ala Gln Pro
    160                 165                 170

TAAG                                                                   534
```

(2) INFORMATION FOR SEQ ID NO:30:

(i) SEQUENCE CHARACTERISTICS:
        (A) LENGTH: 177 amino acids
        (B) TYPE: amino acid
        (D) TOPOLOGY: linear (xi) SEQUENCE DESCRIPTION: SEQ ID NO:30:

```
Thr Pro Leu Gly Pro Ala Ser Ser Leu Pro Gln Ser Phe Leu Leu Lys
```

|   |   |   |   |   |   |   |   |   |   |   |   |   |   |   |
|---|---|---|---|---|---|---|---|---|---|---|---|---|---|---|
| 1 |   |   |   | 5 |   |   |   |   | 10 |   |   |   |   | 15 |

Cys Leu Glu Gln Val Arg Lys Ile Gln Gly Asp Gly Ala Ala Leu Gln
            20                      25                      30

Glu Lys Leu Val Ser Glu Cys Ala Thr Tyr Lys Leu Cys His Pro Glu
            35                      40                      45

Glu Leu Val Leu Leu Gly His Ser Leu Gly Ile Pro Trp Ala Pro Leu
            50                      55                      60

Ser Ser Cys Pro Ser Gln Ala Leu Gln Leu Ala Gly Cys Leu Ser Gln
65                      70                      75                      80

Leu His Ser Gly Leu Phe Leu Tyr Gln Gly Leu Leu Gln Ala Leu Glu
            85                      90                      95

Gly Ile Ser Pro Glu Leu Gly Pro Thr Leu Asp Thr Leu Gln Leu Asp
            100                     105                     110

Val Ala Asp Phe Ala Thr Thr Ile Trp Gln Gln Met Glu Glu Leu Gly
            115                     120                     125

Met Ala Pro Ala Leu Gln Pro Thr Gln Gly Ala Met Pro Ala Phe Ala
            130                     135                     140

Ser Ala Phe Gln Arg Arg Ala Gly Gly Val Leu Val Ala Ser His Leu
145                     150                     155                     160

Gln Ser Phe Leu Glu Val Ser Tyr Arg Val Leu Arg His Leu Ala Gln
            165                     170                     175

Pro ( 2 ) INFORMATION FOR SEQ ID NO:31:

( i ) SEQUENCE CHARACTERISTICS:
        ( A ) LENGTH: 174 amino acids
        ( B ) TYPE: amino acid
        ( D ) TOPOLOGY: linear ( x i ) SEQUENCE DESCRIPTION: SEQ ID NO:31:

Thr Pro Leu Gly Pro Ala Ser Ser Leu Pro Gln Ser Phe Leu Leu Lys
1                       5                       10                      15

Cys Leu Glu Gln Val Arg Lys Ile Gln Gly Asp Gly Ala Ala Leu Gln
            20                      25                      30

Glu Lys Leu Cys Ala Thr Tyr Lys Leu Cys His Pro Glu Glu Leu Val
            35                      40                      45

Leu Leu Gly His Ser Leu Gly Ile Pro Trp Ala Pro Leu Ser Ser Cys
            50                      55                      60

Pro Ser Gln Ala Leu Gln Leu Ala Gly Cys Leu Ser Gln Leu His Ser
65                      70                      75                      80

Gly Leu Phe Leu Tyr Gln Gly Leu Leu Gln Ala Leu Glu Gly Ile Ser
            85                      90                      95

Pro Glu Leu Gly Pro Thr Leu Asp Thr Leu Gln Leu Asp Val Ala Asp
            100                     105                     110

Phe Ala Thr Thr Ile Trp Gln Gln Met Glu Glu Leu Gly Met Ala Pro
            115                     120                     125

Ala Leu Gln Pro Thr Gln Gly Ala Met Pro Ala Phe Ala Ser Ala Phe
            130                     135                     140

Gln Arg Arg Ala Gly Gly Val Leu Val Ala Ser His Leu Gln Ser Phe
145                     150                     155                     160

Leu Glu Val Ser Tyr Arg Val Leu Arg His Leu Ala Gln Pro
            165                     170

( 2 ) INFORMATION FOR SEQ ID NO:32:

-continued ( i ) SEQUENCE CHARACTERISTICS:
    ( A ) LENGTH: 24 base pairs
    ( B ) TYPE: nucleic acid
    ( C ) STRANDEDNESS: single
    ( D ) TOPOLOGY: linear ( x i ) SEQUENCE DESCRIPTION: SEQ ID NO:32:

AATTCGCATG CGGATCCATC GATC    24

( 2 ) INFORMATION FOR SEQ ID NO:33:

( i ) SEQUENCE CHARACTERISTICS:
    ( A ) LENGTH: 24 base pairs
    ( B ) TYPE: nucleic acid
    ( C ) STRANDEDNESS: single
    ( D ) TOPOLOGY: linear ( x i ) SEQUENCE DESCRIPTION: SEQ ID NO:33:

CCGAGATCGA TGGATCCGCA TGCG    24

( 2 ) INFORMATION FOR SEQ ID NO:34:

( i ) SEQUENCE CHARACTERISTICS:
    ( A ) LENGTH: 72 base pairs
    ( B ) TYPE: nucleic acid
    ( C ) STRANDEDNESS: single
    ( D ) TOPOLOGY: linear ( x i ) SEQUENCE DESCRIPTION: SEQ ID NO:34:

TCGACATTAT ATTACTAATT AATTGGGGAC CCTAGAGGTC CCCTTTTTTA TTTTAAAAAG    60

CATGCGGATC CC    72

( 2 ) INFORMATION FOR SEQ ID NO:35:

( i ) SEQUENCE CHARACTERISTICS:
    ( A ) LENGTH: 72 base pairs
    ( B ) TYPE: nucleic acid
    ( C ) STRANDEDNESS: single
    ( D ) TOPOLOGY: linear ( x i ) SEQUENCE DESCRIPTION: SEQ ID NO:35:

CAAGGGGATC CGCATGCTTT TTAAAATAAA AAAGGGGACC TCTAGGGTCC CCAATTAATT    60

AGTAATATAA TG    72